(12) United States Patent
Watanabe et al.

(10) Patent No.: US 10,948,442 B2
(45) Date of Patent: Mar. 16, 2021

(54) IMPEDANCE MEASURING SEMICONDUCTOR CIRCUIT AND BLOOD-SUGAR LEVEL METER

(71) Applicant: Renesas Electronics Corporation, Tokyo (JP)

(72) Inventors: Kunihiko Watanabe, Tokyo (JP); Gaku Masumoto, Tokyo (JP); Kazuo Okado, Tokyo (JP)

(73) Assignee: RENESAS ELECTRONICS CORPORATION, Tokyo (JP)

( * ) Notice: Subject to any disclaimer, the term of this patent is extended or adjusted under 35 U.S.C. 154(b) by 126 days.

(21) Appl. No.: 16/129,578

(22) Filed: Sep. 12, 2018

(65) Prior Publication Data

US 2019/0113472 A1  Apr. 18, 2019

(30) Foreign Application Priority Data

Oct. 18, 2017  (JP) .............................. JP2017-201532

(51) Int. Cl.
| | |
|---|---|
| *G01N 27/02* | (2006.01) |
| *G01N 33/487* | (2006.01) |
| *G01N 33/66* | (2006.01) |
| *C12Q 1/00* | (2006.01) |
| *G01N 27/327* | (2006.01) |

(52) U.S. Cl.
CPC ........... *G01N 27/028* (2013.01); *C12Q 1/006* (2013.01); *G01N 27/3272* (2013.01); *G01N 27/3273* (2013.01); *G01N 27/3274* (2013.01); *G01N 33/48707* (2013.01); *G01N 33/66* (2013.01)

(58) Field of Classification Search
CPC ....... G01N 27/028; G01N 33/66; C12Q 1/006
See application file for complete search history.

(56) References Cited

U.S. PATENT DOCUMENTS

| | | | | |
|---|---|---|---|---|
| 6,085,576 A | * | 7/2000 | Sunshine ........... | G01N 33/0031 73/29.01 |
| 6,446,488 B1 | * | 9/2002 | Kurokawa .......... | F02D 41/1455 73/23.32 |
| 6,645,368 B1 | * | 11/2003 | Beaty ................. | G01N 27/3274 205/792 |

(Continued)

FOREIGN PATENT DOCUMENTS

| | | |
|---|---|---|
| JP | 2007-507711 A | 3/2007 |
| JP | 2016-200588 A | 12/2016 |

(Continued)

*Primary Examiner* — Walter L Lindsay, Jr.
*Assistant Examiner* — Milton Gonzalez
(74) *Attorney, Agent, or Firm* — McDermott Will & Emery LLP

(57) ABSTRACT

An impedance measuring semiconductor circuit that measures impedance of a specimen. The impedance measuring semiconductor circuit includes an operational amplifier, a resistance coupled between a negative input terminal and an output terminal of the operational amplifier, a D/A converter coupled to a positive input terminal, a switch; an A/D converter that is coupled with the output terminal of the operational amplifier and a one-side terminal of a specimen and measures an output voltage from the operational amplifier and a one-side terminal voltage, and a controller that controls an output voltage from the D/A converter based on a one-side terminal voltage measured by the A/D converter.

19 Claims, 12 Drawing Sheets

(56) References Cited

U.S. PATENT DOCUMENTS

| | | | | |
|---|---|---|---|---|
| 6,953,693 B2* | 10/2005 | Neel | ................... | C12Q 1/006 |
| | | | | 204/403.02 |
| 7,540,947 B2* | 6/2009 | Ueno | ................... | C12Q 1/001 |
| | | | | 204/403.01 |
| 8,535,497 B2 | 9/2013 | Fujiwara et al. | | |
| 8,916,036 B2* | 12/2014 | Wang | ................ | G01N 27/3272 |
| | | | | 204/403.02 |
| 9,140,683 B2* | 9/2015 | Cherian | ........... | G01N 33/48785 |
| 9,952,197 B2 | 4/2018 | Saeda et al. | | |
| 2002/0133064 A1* | 9/2002 | Ueno | .............. | G01N 33/48792 |
| | | | | 600/316 |
| 2004/0234943 A1* | 11/2004 | Lepple-Wienhues | ........................ | |
| | | | | G01N 33/48728 |
| | | | | 435/4 |
| 2005/0067277 A1 | 3/2005 | Pierce et al. | | |
| 2015/0068926 A1* | 3/2015 | Ainger | ................ | G01N 33/492 |
| | | | | 205/792 |
| 2016/0003764 A1* | 1/2016 | Beaty, Jr. | ........... | G01N 27/3274 |
| | | | | 205/777.5 |
| 2016/0033440 A1* | 2/2016 | Cho | ................... | G01N 33/49 |
| | | | | 205/782 |
| 2016/0290910 A1 | 10/2016 | Saeda et al. | | |

FOREIGN PATENT DOCUMENTS

| | | |
|---|---|---|
| JP | 2016-200589 A | 12/2016 |
| WO | WO 2005/054840 A1 | 6/2005 |

* cited by examiner

FIG. 11

| | CURRENT DIRECTION | Vt1 < Vtarget | Vt1 ≥ Vtarget |
|---|---|---|---|
| FIRST CASE | DIRECTION A (T1a→T1b) | INCREASE DAC1 | DECREASE DAC1 |
| SECOND CASE | DIRECTION B (T1b→T1a) | DECREASE DAC1 | INCREASE DAC1 |
| THIRD CASE | DIRECTION A (T1a→T1b) | DECREASE DAC2 | INCREASE DAC2 |
| FOURTH CASE | DIRECTION B (T1b→T1a) | INCREASE DAC2 | DECREASE DAC2 |

IMPEDANCE MEASURING SEMICONDUCTOR CIRCUIT AND BLOOD-SUGAR LEVEL METER

CROSS-REFERENCE TO RELATED APPLICATIONS

The disclosure of Japanese Patent Application No. 2017-201532 filed on Oct. 18, 2017 including the specification, drawings and abstract is incorporated herein by reference in its entirety.

BACKGROUND

The present invention relates to an impedance measuring semiconductor circuit and a blood-sugar level meter and more particularly to an impedance measuring semiconductor circuit and a blood-sugar level meter capable of accurately measuring impedances and blood-sugar levels of a specimen such as a test strip.

Patent literatures 1 through 4 describe a biosensor whose electrode is coated with enzyme. The biosensor according to patent literatures 1 through 4 includes one-side terminal and the different-side terminal. A voltage is applied between both terminals of the biosensor to measure a blood-sugar level in blood, for example.

Patent Literature 1: Japanese Unexamined Patent Application Publication No. 2016-200588
Patent Literature 2: Japanese Unexamined Patent Application Publication No. 2016-200589
Patent Literature 3: International Unexamined Patent Application No. 2005/054840
Patent Literature 4: Japanese Translation of Unexamined PCT Application No. 2007-507711

SUMMARY

A measured voltage may contain an error due to on-resistance when an element such as a switch is provided for a current pathway of a measuring circuit that measures blood-sugar levels.

These and other objects and novel features may be readily ascertained by referring to the following description of the present specification and appended drawings.

According to an embodiment, an impedance measuring semiconductor circuit measures impedance of a specimen having a one-side terminal and a different-side terminal and includes: an operational amplifier; a resistance coupled between a negative input terminal of the operational amplifier and an output terminal of the operational amplifier; a D/A converter coupled to a positive input terminal of the operational amplifier; a switch placed between the one-side terminal and the negative input terminal; an A/D converter that is coupled with an output terminal of the operational amplifier and the one-side terminal and measures an output voltage from the operational amplifier and a one-side terminal voltage as a terminal voltage of the one-side terminal; and a controller that controls an output voltage from the D/A converter based on the one-side terminal voltage measured by the A/D converter. A different-side terminal voltage as a terminal voltage of the different-side terminal is set to a predetermined voltage. An output voltage from the operational amplifier is used to measure impedance of the specimen.

The above-mentioned embodiment can provide an impedance measuring semiconductor circuit and a blood-sugar level meter capable of improving the accuracy of measuring the impedance of a specimen, reducing an area in an analog front-end LSI chip, and reducing the LSI chip size.

BRIEF DESCRIPTION OF THE DRAWINGS

FIG. 11 is a diagram illustrating operation of the impedance measuring semiconductor circuit according to the fourth embodiment;

DETAILED DESCRIPTION

Figure 1:
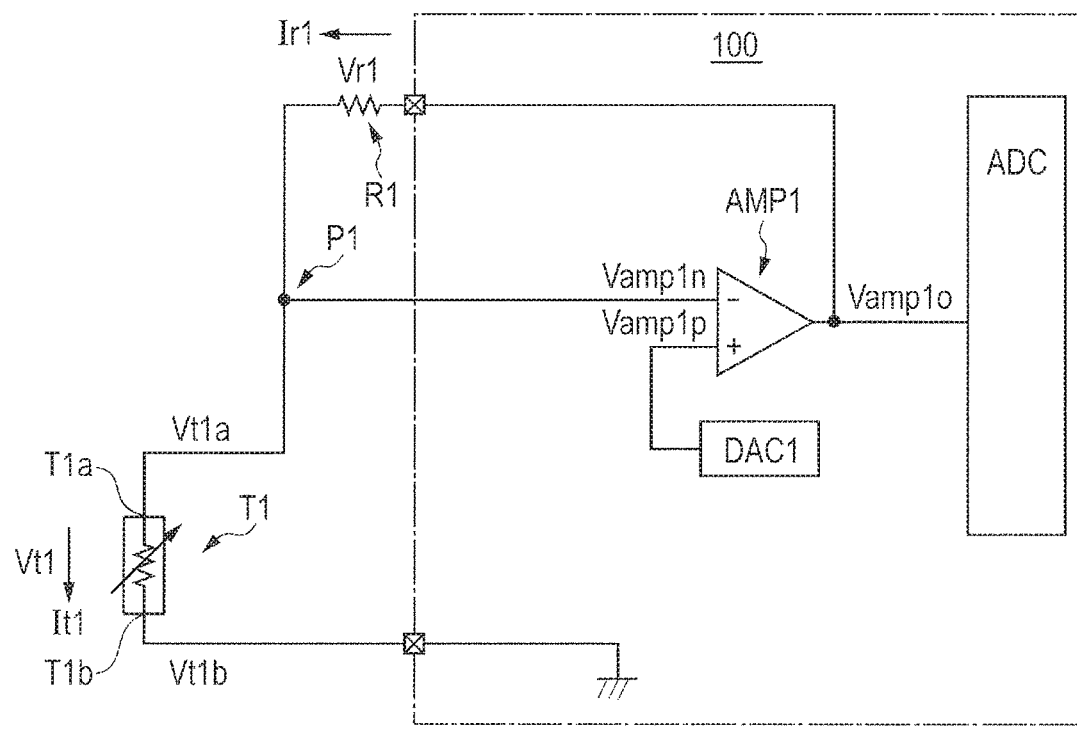
FIG. 1 is a circuit diagram illustrating a configuration of an impedance measuring semiconductor circuit according to a comparative example.

The following description and drawings are omitted and simplified as needed in order to clarify the explanation. In the drawings, mutually corresponding elements are designated by the same reference symbols and a duplicate explanation is omitted as needed.

Firstly, a comparative example is used to explain a measurement error found by the inventors with respect to an impedance measuring semiconductor circuit. This will moreover clarify the impedance measuring semiconductor circuit according to each embodiment.

Comparative Example

The description below first explains a configuration of the impedance measuring semiconductor circuit according to the comparative example. FIG. 1 is a circuit diagram illustrating the configuration of the impedance measuring semiconductor circuit according to the comparative example. As illustrated in FIG. 1, an impedance measuring semiconductor circuit 100 according to the comparative example includes an operational amplifier AMP1, a D/A converter DAC1, a feedback resistance R1, and an A/D converter ADC. The impedance measuring semiconductor circuit 100 measures impedance of a specimen having one-side terminal T1$a$ and a different-side terminal T1$b$.

The operational amplifier AMP1 includes a positive input terminal, a negative input terminal, and an output terminal. The operational amplifier AMP1 outputs output voltage Vamp1$o$ from the output terminal by using positive input voltage Vamp1$p$ input to the positive input terminal and negative input voltage Vamp1$n$ input to the negative input terminal. The D/A converter DAC1 is coupled to the positive input terminal of the operational amplifier AMP1. One end of the resistance R1 is coupled to the negative input terminal of the operational amplifier AMP1. The other end of the resistance R1 is coupled to the output terminal of the operational amplifier AMP1. The A/D converter ADC is coupled to the output terminal of the operational amplifier AMP1.

The resistance R1 is coupled between the negative input terminal of the operational amplifier AMP1 and the output terminal of the operational amplifier AMP1. The resistance R1 is provided as a feedback resistance for the operational amplifier AMP1.

The D/A converter DAC1 is coupled to the positive input terminal of the operational amplifier AMP1. The D/A converter DAC1 outputs a predetermined voltage to the positive input terminal of the operational amplifier AMP1.

The A/D converter ADC is coupled to the output terminal of the operational amplifier AMP1. The A/D converter ADC measures an output voltage from the operational amplifier AMP1.

The specimen is provided as a test strip T1, for example. The description below assumes the specimen to be the test strip T1. The specimen is not limited to the test strip T1 but may be provided as a biosensor when the one-side terminal T1$a$ and the different-side terminal T1$b$ are included. A measurement target such as a blood-sugar level is measured by using the test strip T1 as a specimen. The test strip T1 includes a sensor whose electrode is coated with enzyme. The impedance of the test strip T1 changes when a drop of blood is applied to the electrode of the test strip T1. The change in the impedance is used to measure a reaction between the enzyme and the blood.

Specifically, a voltage is applied between the one-side terminal T1$a$ and the different-side terminal T1$b$ of the test strip T1 having the electrode to which a drop of blood is applied. An electric charge is then generated, allowing an electric current to flow. A charge amount is measured from a total amount of the current. A blood-sugar level correlated with the charge amount is thereby measured.

The one-side terminal T1$a$ of the test strip T1 is coupled to the resistance R1. The one-side terminal T1$a$ of test strip T1 is coupled to the negative input terminal of the operational amplifier AMP1. The one-side terminal T1$a$ of the test strip T1 is coupled to a contact point P1 along a wiring that couples the resistance R1 with the negative input terminal of the operational amplifier AMP1. The different-side terminal T1$b$ of the test strip T1 is grounded.

Operation of the impedance measuring semiconductor circuit 100 will be described. The D/A converter DAC1 is forced to input a predetermined voltage to the positive input terminal of the operational amplifier AMP1. A voltage is thereby applied to the test strip T1. For example, a voltage of several hundreds of millivolts to several volts is applied between both terminals of the test strip T1. A current It1 of several hundreds of microamperes then flows through the test strip T1.

Figure 2:
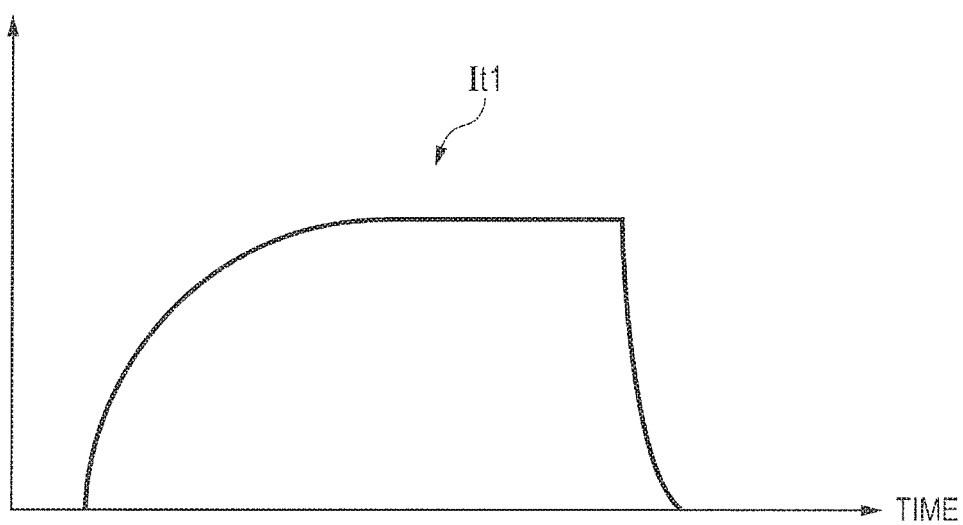
FIG. 2 is a graph illustrating a current flowing through a test strip using an impedance measuring semiconductor circuit, in which the horizontal axis represents the time and the vertical axis represents a current.

FIG. 2 is a graph illustrating a current flowing through the test strip T1 using the impedance measuring semiconductor circuit, in which the horizontal axis represents the time and the vertical axis represents a current. As illustrated in FIG. 2, applying a predetermined voltage between both terminals of the test strip T1 generates a charge at the test strip, allowing the current It1 to flow. The current It1 increases as the time elapses. The total amount of generated charge is found from values of integral for the current It1 during a predetermined time period. A blood-sugar level correlated to the total amount of charge is calculated.

The current It1 flowing through the test strip T1 is equal to the current Ir1 flowing through resistance R1. It is therefore possible to measure the current It1 flowing through the test strip T1 by measuring the current Ir1 flowing through resistance R1. Measuring a current flowing through the resistance R1 requires measuring a voltage Vr1 applied to both ends of the resistance R1. The voltage Vr1 applied to both ends of the resistance R1 is measured by measuring an output voltage from the operational amplifier AMP1 using the A/D converter ADC. The current It1 flowing through the test strip T1 can be found by dividing the measured voltage Vr1 by a known resistance value of the resistance R1.

Varying a voltage applied between both terminals of the test strip T1 can vary the magnitude and the direction of the current It1 flowing through the test strip T1. It is therefore possible to measure various parameters such as hematocrit values as well as blood-sugar levels. A voltage at the one-side terminal T1$a$ is referred to as a one-side terminal voltage Vt1$a$. A voltage at the different-side terminal T1$b$ is referred to as a different-side terminal voltage Vt1$b$. A voltage applied between both terminals of the test strip T1 is referred to as a terminal-to-terminal voltage Vt1. When the different-side terminal T1$b$ is grounded, the terminal-to-terminal voltage Vt1 is equal to the one-side terminal voltage Vt1$a$.

Figure 3:
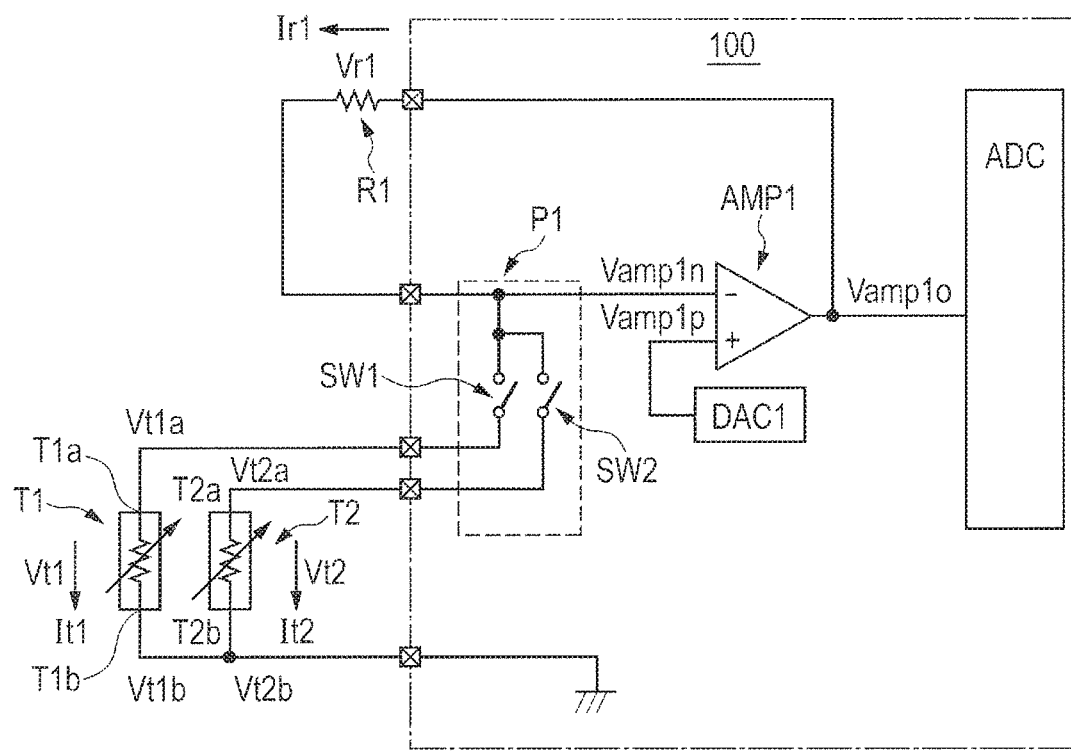
FIG. 3 is a circuit diagram illustrating a configuration to measure a plurality of test strips using the impedance measuring semiconductor circuit according to the comparative example.

FIG. 3 is a circuit diagram illustrating a configuration to measure a plurality of test strips using the impedance measuring semiconductor circuit according to the comparative example. When there is a plurality of test strips T1 and T2 as illustrated in FIG. 3, the test strips T1 and T2 are provided for the impedance measuring semiconductor circuit 100. The analog switches SW1 and SW2 are coupled to the test strips T1 and T2. The analog switch is also simply referred to as a switch.

Specifically, the one-side terminal T1a of the test strip T1 is coupled to the resistance R1 and the negative input terminal of the operational amplifier AMP1 via the switch SW1. The switch SW1 is coupled between the one-side terminal T1a of the test strip T1 and the contact point P1. The switch SW1 is therefore placed between the one-side terminal T1a of the test strip T1 and the negative input terminal. The different-side terminal T1b of the test strip T1 is grounded.

The one-side terminal T2a of the test strip T2 is coupled to the resistance R1 and the negative input terminal of the operational amplifier AMP1 via the switch SW2. The switch SW2 is coupled between the one-side terminal T2a of the test strip T2 and the contact point P1. The switch SW2 is therefore placed between the one-side terminal T2a of the test strip T2 and the negative input terminal. The different terminal T2b of the test strip T2 is grounded. As for the rest, the operational amplifier AMP1, the D/A converter DAC1, the feedback resistance R1, and the A/D converter ADC are configured similarly to those in FIG. 1.

Each of the test strips T1 and T2 is measured by selecting each of the switches SW1 and SW2. Measuring the test strip T1 requires turning on the switch SW1 and turning off the switch SW2. A current flowing through the resistance R1 is measured by measuring the voltage Vr1 applied to both ends of the resistance R1. As above, the current It1 flowing through the test strip T1 is measured.

Measuring the test strip T2 requires turning on the switch SW2 and turning off the switch SW1. A current flowing through the resistance R1 is measured by measuring the voltage Vr1 applied to both ends of the resistance R1. As above, the current It2 flowing through the test strip T2 is measured.

When the current It1 and the current It2 are measured, the voltage Vr1 applied to both ends of the resistance R1 contains a voltage applied to both ends of the switches SW1 and SW2 in addition to the terminal-to-terminal voltages Vt1 and Vt2 for the test strip T1 and the test strip T2. Therefore, accurately measuring the currents It1 and It2 flowing through the test strip T1 and the test strip T2 needs to take into account a voltage drop due to an on-resistance of the switches SW1 and SW2.

An available method of taking into account an on-resistance of the switches SW1 and SW2 is to couple a highly accurate resistance having a highly accurately measured resistance value instead of the test strips T1 and T2 for measurement and calibration. However, this method provides the calibration based on a predetermined resistance value. Accurate calibration is therefore difficult even when the method is applied to a case where the currents It1 and It2 flowing through the test strips T1 and T2 vary and the impedance of the test strips T1 and T2 varies.

As above, measuring the test strips T1 and T2 requires the switches SW1 and SW2 to select each of the test strips T1 and T2. However, the resistance component of the switch SW1, for example, causes a measurement error. There is a variation in the resistance of the switch SW1, for example. Measuring the test strip T1, for example, includes the varied resistance of the switch SW1, for example.

Therefore, ideally, the resistance of the switch SW1, for example, favorably approximates to zero ohms. At least one of the operational amplifier AMP1, the A/D converter ADC, the D/A converter DAC1, and the switch SW1, for example, is formed to include the CMOS structure formed over a semiconductor substrate. Accordingly, the switch SW1, for example, is also formed in accordance with a CMOS fabrication process. It is necessary to increase an area occupied by the switch SW1, for example, over a chip in order to provide the switch SW1, for example, having the resistance approximate to zero ohms by using the CMOS fabrication process. In this case, the chip size cannot be reduced.

Increasing measurement targets in addition to the blood-sugar level complicates the measurement. The number of the switches SW1, for example, increases accordingly. Therefore, the chip size further increases.

Therefore, there is a demand for the impedance measuring semiconductor circuit capable of improving the accuracy of measuring the impedance of the test strip T1, for example, reducing an area in the chip, and reducing the chip size.

First Embodiment

The description below explains the impedance measuring semiconductor circuit according to the first embodiment. The impedance measuring semiconductor circuit according to the present embodiment can improve the accuracy of measuring the impedance of a specimen, reduce an area in the chip, and reduce the chip size.

(Configuration of the Impedance Measuring Semiconductor Circuit)

Figure 4:
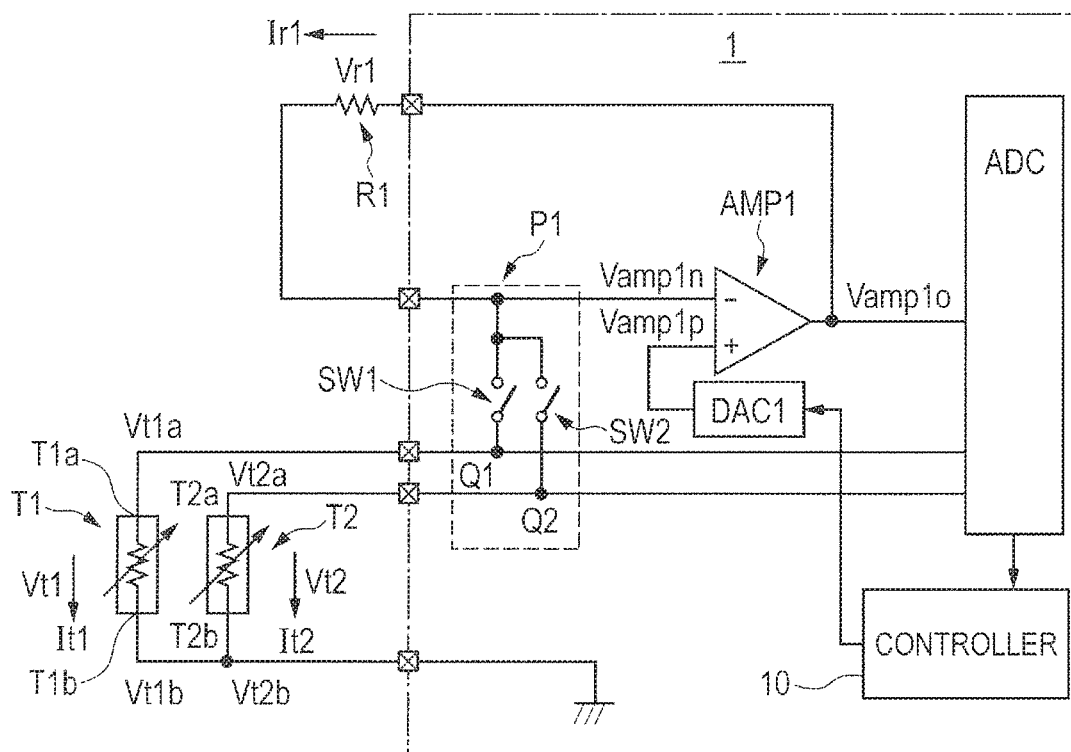
FIG. 4 is a circuit diagram illustrating a configuration of an impedance measuring semiconductor circuit according to a first embodiment.

The configuration of the impedance measuring semiconductor circuit according to the present embodiment will be first described. Operation of the impedance measuring semiconductor circuit will be then described. FIG. 4 is a circuit diagram illustrating the configuration of the impedance measuring semiconductor circuit according to the first embodiment.

As illustrated in FIG. 4, an impedance measuring semiconductor circuit 1 includes the operational amplifier AMP1, the D/A converter DAC1, the feedback resistance R1, the A/D converter ADC, the switches SW1 and SW2, and a controller 10. The impedance measuring semiconductor circuit 1 may include an operation part that calculates a blood-sugar level from the measured impedance. The impedance measuring semiconductor circuit 1 measures the impedance of a specimen. The impedance measuring semiconductor circuit 1 will be described by using an analog front-end as an example. The impedance measuring semiconductor circuit 1 may be formed over a semiconductor substrate (semiconductor chip) such as monocrystalline silicon by using the CMOS fabrication process.

The operational amplifier AMP1 includes the positive input terminal, the negative input terminal, and the output terminal. The operational amplifier AMP1 outputs output voltage Vamp1o from the output terminal by using positive input voltage Vamp1p input to the positive input terminal and negative input voltage Vamp1n input to the negative input terminal. The D/A converter DAC1 is coupled to the positive input terminal of the operational amplifier AMP1. One end of the resistance R1 is coupled to the negative input terminal of the operational amplifier AMP1. The other end of the resistance R1 is coupled to the output terminal of the operational amplifier AMP1. The A/D converter ADC is coupled to the output terminal of the operational amplifier AMP1.

The resistance R1 is coupled between the negative input terminal of the operational amplifier AMP1 and the output terminal of the operational amplifier AMP1. The resistance R1 is provided as a feedback resistance for the operational amplifier AMP1.

The D/A converter DAC1 is coupled to the positive input terminal of the operational amplifier AMP1. The controller 10 controls an output voltage from the D/A converter DAC1. Under control of the controller 10, the D/A converter DAC1 outputs a predetermined voltage to the positive input terminal of the operational amplifier AMP1.

The A/D converter ADC is coupled to the output terminal of the operational amplifier AMP1. The A/D converter ADC measures an output voltage from the operational amplifier AMP1. The A/D converter ADC transmits information about the measured output voltage from the operational amplifier AMP1 to the controller 10.

The A/D converter ADC is coupled with one-side terminal T1a of each test strip T1, for example. The A/D converter ADC thereby measures the one-side terminal voltage Vt1a at one-side terminal T1a of each test strip T1, for example. The A/D converter ADC transmits information about the measured one-side terminal voltage Vt1a of each test strip T1, for example, to the controller 10.

The test strip T1, for example, is assumed to be a measurement target. The test strip T1, for example, includes the one-side terminal T1a and the different-side terminal T1b, for example. The use of the test strip T1, for example, can measure a blood-sugar level, for example. Configurations of the test strips T1 and T2 are similar to those described above.

The one-side terminal T1a of the test strip T1 is coupled to the resistance R1 via the switch SW1. The one-side terminal T1a of the test strip T1 is coupled to the negative input terminal of the operational amplifier AMP1 via the switch SW1.

The one-side terminal T1a of the test strip T1 is coupled, via the switch SW1, to the contact point P1 along the wiring that couples the resistance R1 with the negative input terminal of the operational amplifier AMP1. Namely, the switch SW1 is provided between the one-side terminal T1a and the contact point P1. The switch SW1 is therefore provided between the one-side terminal T1a of the test strip T1 and the negative input terminal.

The one-side terminal T1a of the test strip T1 is coupled to the A/D converter ADC. The switch SW1 is provided between the contact point P1 and the contact point Q1 along a wiring that couples the one-side terminal T1a of the test strip T1 with the A/D converter ADC. The different-side terminal T1b of the test strip T1 is grounded. The different-side terminal voltage Vt1b is thereby set to a predetermined voltage.

The one-side terminal T2a of the test strip T2 is coupled to the resistance R1 via the switch SW2. The one-side terminal T2a of the test strip T2 is coupled to the negative input terminal of the operational amplifier AMP1 via the switch SW2.

The one-side terminal T2a of the test strip T2 is coupled, via the switch SW2, to the contact point P1 along the wiring that couples the resistance R1 with the negative input terminal of the operational amplifier AMP1. Namely, the switch SW2 is provided between the one-side terminal T2a and the contact point P1. The switch SW2 is therefore provided between the one-side terminal T2a of the test strip T2 and the negative input terminal.

The one-side terminal T2a of the test strip T2 is coupled to the A/D converter ADC. The switch SW2 is provided between the contact point P1 and the contact point Q2 along the wiring that couples the one-side terminal T2a of the test strip T2 with the A/D converter ADC. The different-side terminal T2b of the test strip T2 is grounded. The different-side terminal voltage Vt2b is thereby set to a predetermined voltage.

The controller 10 controls an output voltage from the D/A converter DAC1 based on the one-side terminal voltages Vt1a and Vt2a measured by the A/D converter ADC at the test strips T1 and T2. For example, the controller 10 controls the D/A converter DAC1 so that the one-side terminal voltage Vt1a of the test strip T1, for example, reaches a predetermined target value Vtarget. The predetermined target value Vtarget is to be applied to a measurement target such as the test strip T1, for example. A negative input voltage and a positive input voltage to the operational amplifier AMP1 increase by a voltage drop due to the on-resistance of the switch SW1. However, as will be described below, a voltage corresponding to the predetermined target value Vtarget can be applied between both terminals of the test strip T1, for example. A control method for the controller 10 may use a special-purpose sequencer or a microcomputer.

(Operation of the Impedance Measuring Semiconductor Circuit)

Figure 5:
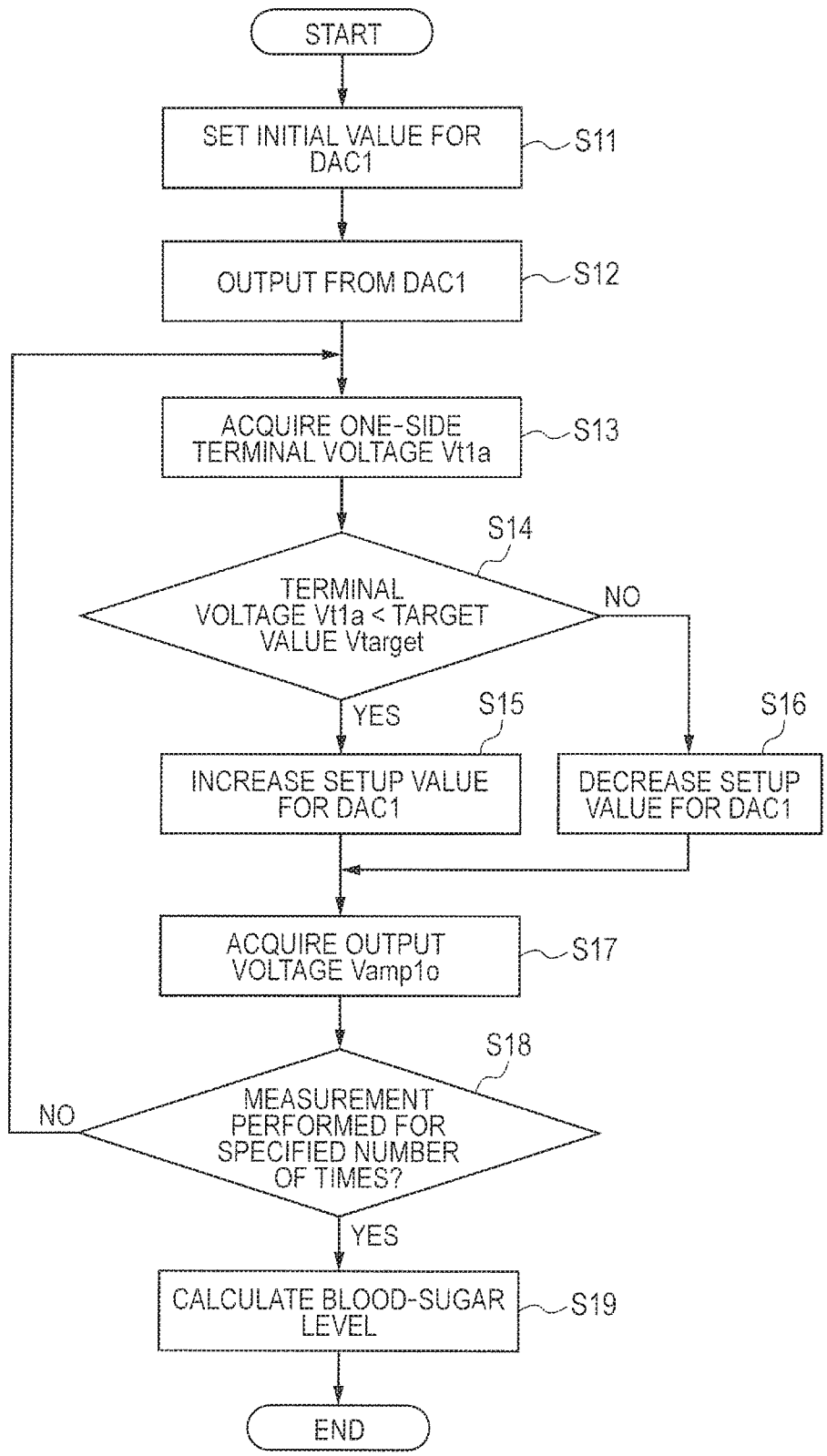
FIG. 5 is a flowchart illustrating operation of the impedance measuring semiconductor circuit according to the first embodiment.

The description below explains operation of the impedance measuring semiconductor circuit 1. FIG. 5 is a flowchart illustrating operation of the impedance measuring semiconductor circuit according to the first embodiment. In FIG. 5, the test strip T1 is used as a specimen to measure impedance and a blood-sugar level of the test strip T1. The switch SW1 is therefore coupled as being turned on and the other switch is not coupled as being turned off. A similar method can be used to measure, for example, impedance of other specimens than the test strip T1.

At step S11 in FIG. 5, the controller 10 sets an initial value for an output voltage from the D/A converter DAC1. The initial value corresponds to the target value Vtarget applied to the test strip T1.

At step S12, the controller 10 controls the D/A converter DAC1 to output the initial value set for the D/A converter DAC1. The D/A converter DAC1 thereby outputs the initial value to the positive output terminal of the operational amplifier AMP1. Virtual ground for the operational amplifier AMP1 then causes the test strip T1 to be applied with a differential voltage between the output voltage from the D/A converter DAC1 and GND.

The initial value for the DAC1 is applied between the test strip T1 and the switch SW1 before a current flows through the test strip T1. The one-side terminal voltage measured by the A/D converter ADC at the test strip T1 is comparable to the output voltage from the D/A converter DAC1.

Immediately after that, as illustrated in FIG. 2, the current starts flowing between the test strip T1 and the switch SW1. A voltage drop thereby occurs due to the on-resistance of the switch SW1. The test strip T1 is therefore applied with a voltage acquired by subtracting the voltage drop for the switch SW1 from the output voltage of the D/A converter DAC1. The A/D converter ADC measures the one-side terminal voltage Vt1a at the test strip T1.

At step S13, the controller 10 acquires the one-side terminal voltage Vt1a of the test strip T1 from the A/D converter ADC.

At step S14, the controller 10 determines whether the acquired one-side terminal voltage Vt1a is lower than the target value Vtarget. The one-side terminal voltage Vt1a may be lower than the predetermined target value Vtarget (Yes). In this case, at step S15, the controller 10 provides control to increase the setup value for the D/A converter DAC1. The output voltage from the D/A converter DAC1 is thereby increased.

At step S14, the one-side terminal voltage Vt1a may be higher than or equal to the target value Vtarget (No). In this case, at step S16, the controller 10 provides control to decrease the setup value for the D/A converter DAC1. The output voltage from the D/A converter DAC1 is thereby decreased.

Suppose the one-side terminal voltage Vt1a is confirmed to fall within a predetermined voltage setup range. At step S17, the controller 10 then uses the A/D converter ADC to acquire the output voltage Vamp1o from the operational amplifier AMP1. The impedance measuring semiconductor circuit 1 measures the impedance of the test strip T1 by using the output voltage Vamp1o from the operational amplifier AMP1.

At step S18, the controller 10 determines whether the measurement is performed for a specified number of times. When the measurement is not performed for a specified number of times (No), the process returns to step S13 and acquires the one-side terminal voltage Vt1a of the test strip T1 by using the A/D converter ADC. The process is repeated from step S13 to step S18. Repeating the process at a specified interval can approximate the one-side terminal voltage Vt1a of the test strip to the target value Vtarget.

When the measurement is performed for a specified number of times (Yes), the process proceeds to step S19 and calculates the blood-sugar level. For example, the operation part calculates the blood-sugar level correlated to the charge amount based on the graph as illustrated in FIG. 2. The process then terminates. As above, the impedance measuring semiconductor circuit 1 measures the impedance of the test strip T1 as a specimen.

Figure 6:
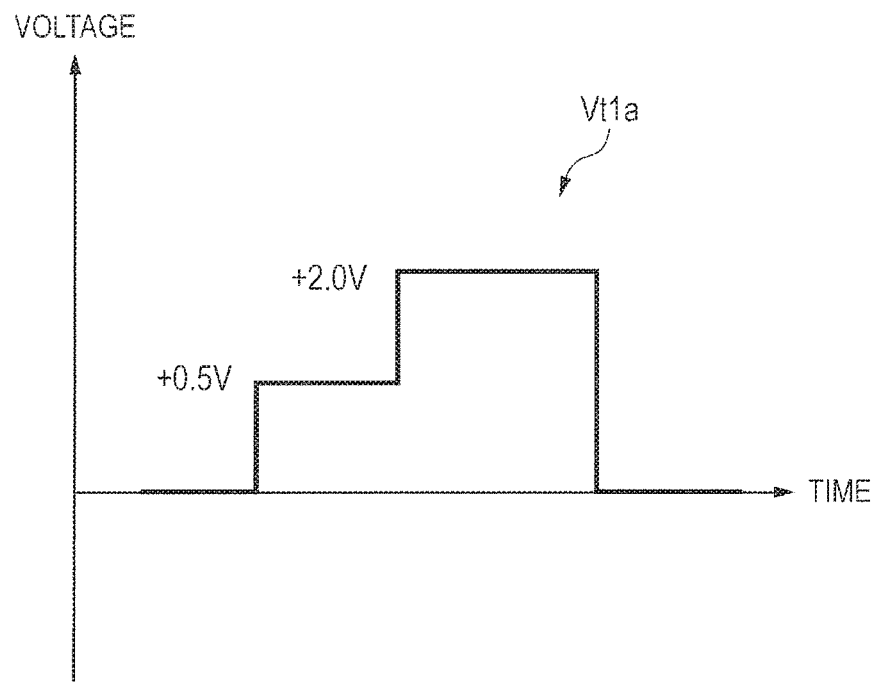
FIG. 6 is a graph illustrating operation of the impedance measuring semiconductor circuit according to the first embodiment, in which the horizontal axis represents the time and the vertical axis represents a voltage at one-side terminal of a test strip.
Figure 7:
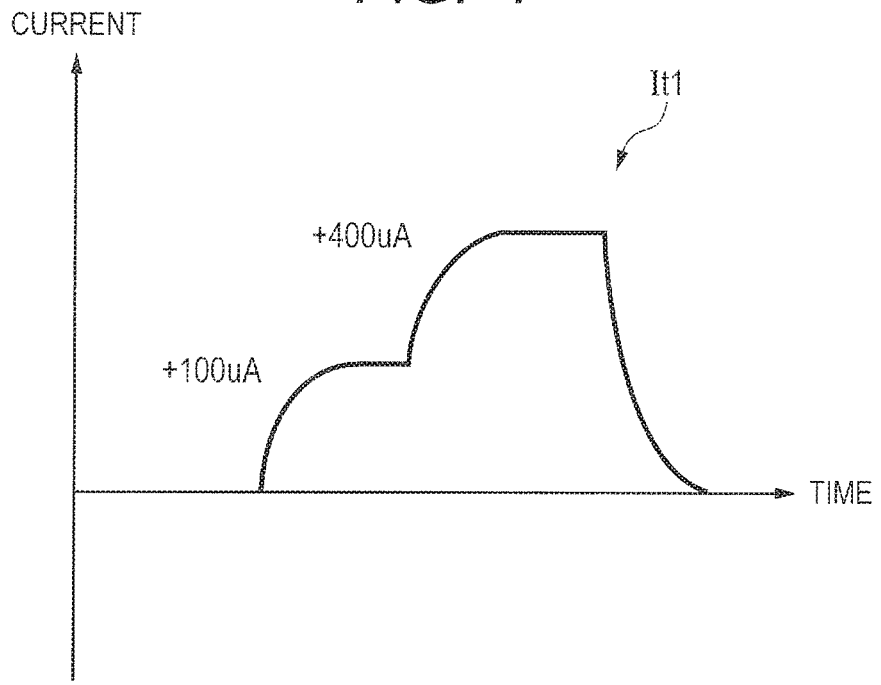
FIG. 7 is a graph illustrating operation of the impedance measuring semiconductor circuit according to the first embodiment, in which the horizontal axis represents the time and the vertical axis represents a current flowing through a test strip.

FIG. 6 is a graph illustrating operation of the impedance measuring semiconductor circuit according to the first embodiment, in which the horizontal axis represents the time and the vertical axis represents a voltage at one-side terminal of a test strip. FIG. 7 is a graph illustrating operation of the impedance measuring semiconductor circuit according to the first embodiment, in which the horizontal axis represents the time and the vertical axis represents a current flowing through a test strip.

Measuring a blood-sugar level at the test strip T1 may require measuring other substances such as a hematocrit value in order to correct the measured blood-sugar level. In order to measure such a different substance, a voltage applied to the test strip T1 is varied stepwise and corresponding values are measured.

As illustrated in FIGS. 6 and 7, for example, the blood-sugar level measurement uses the one-side terminal voltage Vt1a set to +0.5 [V] as a target value. In this case, a current of +100 [μA] flows through the test strip T1. The hematocrit value measurement uses the one-side terminal voltage Vt1a set to +2.0 [V] as a target value. In this case, a current of +400 [μA] flows through the test strip T1.

The present embodiment can versatilely control the magnitude of the one-side terminal voltage Vt1a for the test strip T1 and is therefore applicable to a case where a voltage to be applied varies with a substance or enzyme to be measured.

The switch SW1 is then turned off and the switch SW2 for the test strip T2 is turned on. The same method is used to continue measuring the test strip T2. There is no limitation on a sequence of measuring the test strips. The test strip T1 may be measured after the test strip T2, or otherwise. The measurement terminates when the measurement of the targeted test strip terminates.

An effect of the impedance measuring semiconductor circuit 1 will be described.

The controller 10 of the impedance measuring semiconductor circuit 1 according to the present embodiment controls an output voltage from the D/A converter DAC1 coupled to the positive input terminal of the operational amplifier AMP1 based on the one-side terminal voltage Vt1a for the test strip T1 acquired from the A/D converter ADC. The one-side terminal voltage Vt1a for the test strip T1 can be accurately used as the target value Vtarget. It is therefore possible to improve the accuracy of measuring the impedance of the test strip T1.

The impedance measuring semiconductor circuit 1 according to the present embodiment can suppress an effect of voltage drop due to the on-resistance of the switch SW1. It is therefore possible to decrease an area of the switch SW1 inversely proportional to the square of the on-resistance of the switch SW1. The chip size can be thereby decreased.

For example, the current It1 of 100 [μA] flows through the test strip T1 when a voltage of 0.5 [V] is applied between both terminals of the test strip T1. In this case, supposing that the measurement error to be 0.1[%], the on-resistance value Rsw1 allowed for the switch SW1 is then calculated as Rsw1=0.5/0.0001×0.001=5 [Ω]. The size of the switch SW1, for example, is equal to several hundreds of square micrometers per switch. This area greatly affects on the chip size. Increasing the measurement target and the number of switches further increases an effect on the chip size.

However, the present embodiment can suppress an effect of voltage drop due to the on-resistance of the switch SW1, for example. The chip size can be reduced without the need to decrease the on-resistance of the switch SW1, for example.

Second Embodiment

Figure 8:
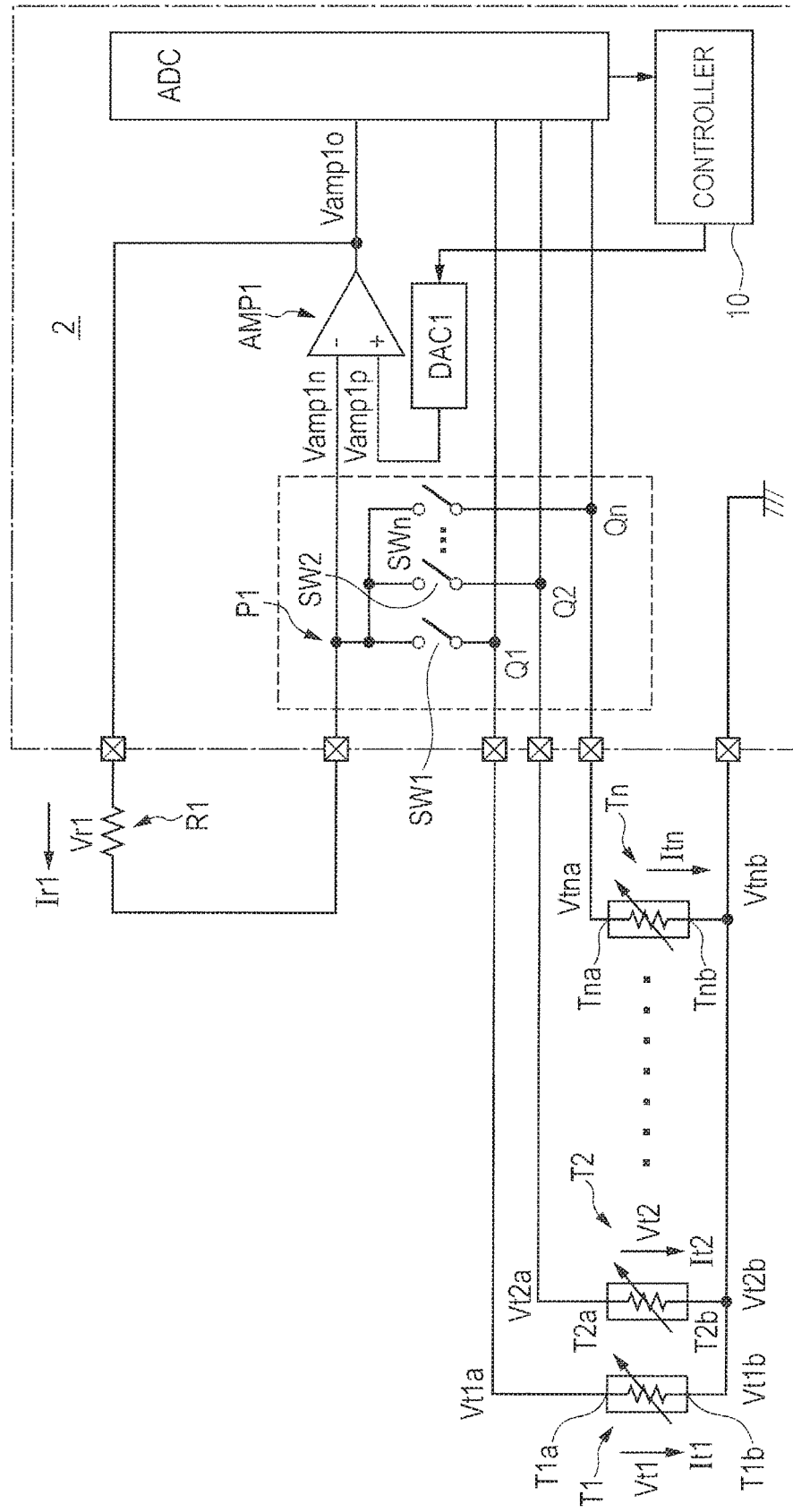
FIG. 8 is a circuit diagram illustrating a configuration of an impedance measuring semiconductor circuit according to a second embodiment.

The impedance measuring semiconductor circuit according to the second embodiment will be described. The impedance measuring semiconductor circuit according to the present embodiment provides an example of using n (three or more) test strips T1. FIG. 8 is a circuit diagram illustrating a configuration of the impedance measuring semiconductor circuit according to the second embodiment.

As illustrated in FIG. 8, an impedance measuring semiconductor circuit 2 includes n test strips T1 through Tn. Each of the n test strips T1 through Tn is coupled to the contact point P1 via the switches SW1 through SWn. The impedance measuring semiconductor circuit 2 is provided with a plurality of test strips T1 as specimens. The switch SW1, for example, is placed between the one-side terminal of each measurement target and the negative input terminal.

Specifically, for example, one-side terminal Tna of the nth test strip Tn out of the test strips T1 through Tn is coupled to the resistance R1 via the switch SWn. The one-side terminal Tna of the test strip Tn is coupled to the negative input terminal of the operational amplifier AMP1 via the switch SWn.

The one-side terminal Tna of the test strip Tn is coupled, via the switch SWn, to the contact point P1 along the wiring that couples the resistance R1 with the negative input terminal of the operational amplifier AMP1. Namely, the switch SWn is provided between the one-side terminal Tna and the contact point P1.

The one-side terminal Tna of the test strip Tn is coupled to the A/D converter ADC. The switch SWn is provided between the contact point P1 and a contact point Qn along a wiring that couples the one-side terminal Tna of the test strip Tn with the A/D converter ADC. A different-side terminal Tnb of the test strip Tn is grounded. The other configurations are equal to the first embodiment.

The operation of the impedance measuring semiconductor circuit 2 is equal to that of the first embodiment except that the impedance measuring semiconductor circuit 2 repeatedly performs the operation of the impedance measuring semiconductor circuit 1 illustrated in FIG. 5 on each of the n test strips Tn.

An effect of the impedance measuring semiconductor circuit 2 according to the second embodiment will be described. The impedance measuring semiconductor circuit 2 includes switch SWn corresponding to each of the n test strips Tn. It is therefore possible to perform complicated measurement containing more types and items, for example. It is also possible to perform accurate measurement on a current flowing through each path for the test strip Tn regardless of on-resistance values of the switch SWn.

It is possible to reduce an area in the chip occupied by the n switches SWn corresponding to the n test strips Tn, for example. The effect of reducing the chip size is more remarkable. The other configurations and effects are contained in the description of the first embodiment.

Third Embodiment

Figure 9:
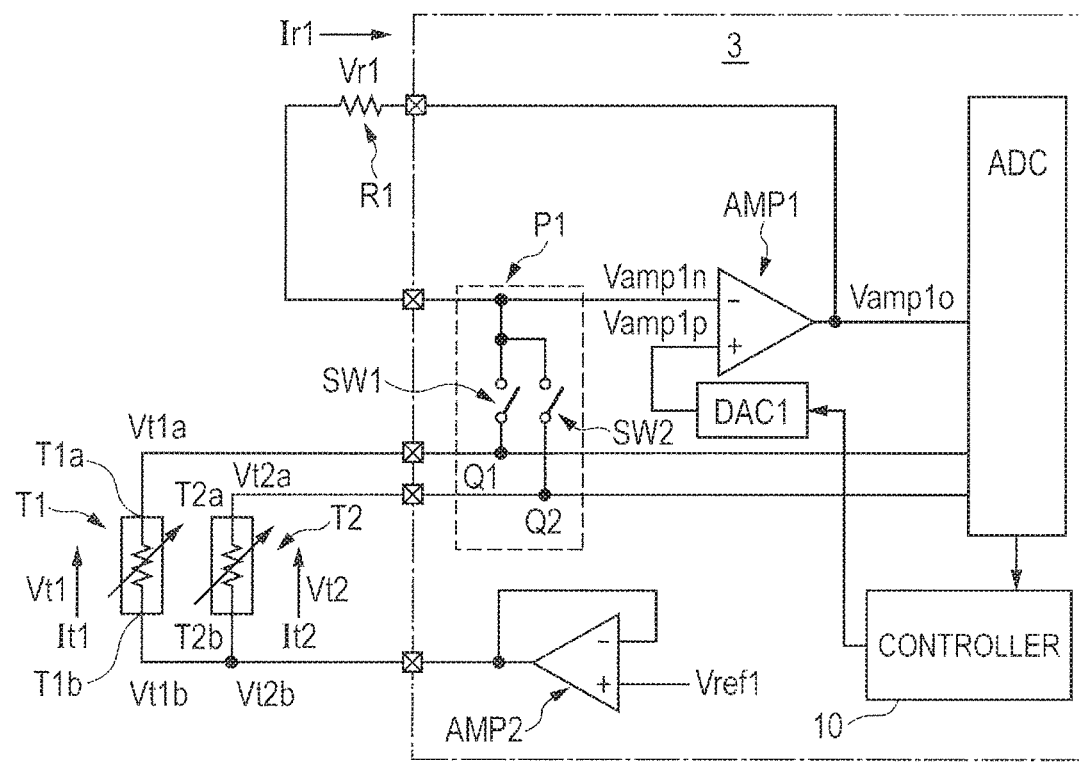
FIG. 9 is a circuit diagram illustrating a configuration of an impedance measuring semiconductor circuit according to a third embodiment.

The impedance measuring semiconductor circuit according to the third embodiment will be described. The impedance measuring semiconductor circuit according to the present embodiment provides an example of reversing the direction of a current flowing through the test strips T1 and T2, for example. FIG. 9 is a circuit diagram illustrating a configuration of the impedance measuring semiconductor circuit according to the third embodiment.

As illustrated in FIG. 9, an impedance measuring semiconductor circuit 3 according to the present embodiment further includes a buffer amplifier AMP2. The buffer amplifier AMP2 includes a positive input terminal, a negative input terminal, and an output terminal. The output terminal of the buffer amplifier AMP2 is coupled to the negative input terminal of the buffer amplifier. A reference voltage is input to the positive input terminal of the buffer amplifier. For example, a reference voltage generator generates a reference voltage Vref1.

In the impedance measuring semiconductor circuit 3 according to the present embodiment, the different-side terminals T1b and T2b of the test strips T1 and T2 are coupled to the output terminal of the buffer amplifier AMP2. The different-side terminal voltages Vt1b and Vt2b of the impedance measuring semiconductor circuit 3 are coupled to the output terminal of the buffer amplifier AMP2 and thereby remain constant. For example, the different-side terminal voltages Vt1b and Vt2b of the test strips T1 and T2 are set to the reference voltage Vref1 by using the buffer amplifier AMP2.

The controller 10 controls the D/A converter DAC1 so that the one-side terminal voltages Vt1a and Vt2a of the test strips T1 and T2 are lower than the different-side terminal voltages Vt1b and Vt2b. This allows the direction of a current flowing through the test strips T1 and T2 to be contrary to the first embodiment. For example, the direction of the current is configured so that the current flows from the different-side terminals T1b and T2b to the one-side terminals T1a and T2a.

As in the first embodiment, the direction of a current flowing from the one-side terminals T1a and T2a to the different-side terminals T1b and T2b is defined as direction A. The direction of a current flowing from the different-side terminals T1b and T2b to the one-side terminals T1a and T2a is defined as direction B.

The description below explains operation of the impedance measuring semiconductor circuit 3 according to the third embodiment. The operation of the impedance measuring semiconductor circuit 3 differs from the operation of the impedance measuring semiconductor circuit 1 only in the direction of a current. A method of finding a blood-sugar level from the impedance can be therefore found based on the flowchart at step S11 through step S19 illustrated in FIG. 5.

An effect of the impedance measuring semiconductor circuit 3 according to the third embodiment will be described. The present embodiment can allow the direction of a current flowing through the test strips T1 and T2 to be contrary to the above-mentioned first and second embodiments. Similarly to the first embodiment, even the reverse current direction can also perform accurate measurement regardless of the on-resistance of the switches SW1 and SW2, for example.

For example, direction A as the current direction can measure oxidation reaction at an electrode. Direction B can measure reduction reaction. The measurement can be applied to various types of reaction of the test strips T1 and T2, for example. Even during the measurement of various types of reaction, a measurement target can be highly accurately measured regardless of the on-resistance of the switches SW1 and SW2. The relation between the current direction and the oxidation reaction or the reduction reaction is not unchangeable. The other configurations and effects are included in the description of the first and second embodiments Fourth Embodiment The impedance measuring semiconductor circuit according to the fourth embodiment will be described. The impedance measuring semiconductor circuit according to the present embodiment controls voltages at both ends of the test strips T1 and T2.

Figure 10:
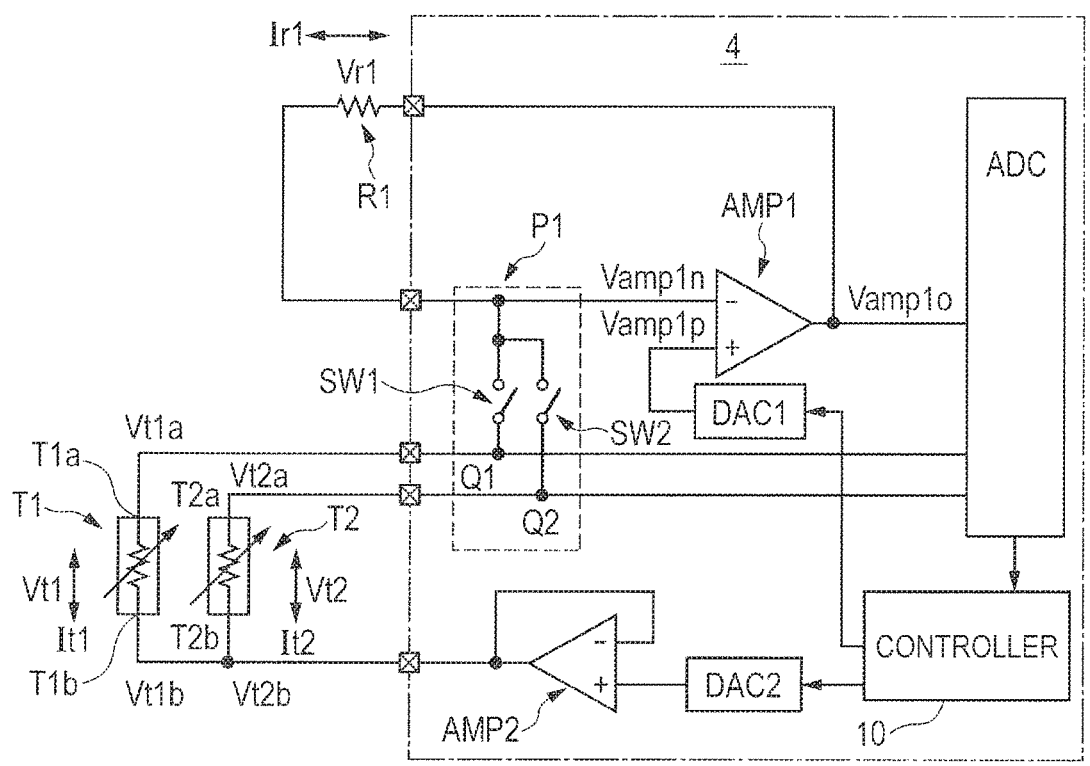
FIG. 10 is a circuit diagram illustrating a configuration of an impedance measuring semiconductor circuit according to a fourth embodiment.

FIG. 10 is a circuit diagram illustrating a configuration of the impedance measuring semiconductor circuit according to the fourth embodiment. As illustrated in FIG. 10, an impedance measuring semiconductor circuit 4 according to the present embodiment includes the operational amplifier AMP1, the buffer amplifier AMP2, a first D/A converter DAC1, a second D/A converter DAC2, the feedback resistance R1, the A/D converter ADC, the switches SW1 and SW2, and the controller 10.

The impedance measuring semiconductor circuit 4 according to the present embodiment differs from the impedance measuring semiconductor circuit 3 according to the third embodiment in the positive input terminal side of the buffer amplifier AMP2. Namely, the second D/A converter DAC2 is coupled to the positive input terminal of the buffer amplifier AMP2. An output voltage from the second D/A converter DAC2 is input instead of the reference voltage Vref1 as input. The D/A converter DAC1 coupled to the positive input terminal of the operational amplifier AMP1 is referred to as the first D/A converter DAC1.

The controller 10 controls at least one of an output voltage from the first D/A converter DAC1 and an output voltage from the second D/A converter DAC2 based on the terminal-to-terminal voltages Vt1 and Vt2 calculated by using the one-side terminal voltages Vt1a and Vt2a measured by the A/D converter ADC at the test strips T1 and T2.

Alternatively, the controller 10 controls the first D/A converter DAC1 and the second D/A converter DAC2 so that the one-side terminal voltages Vt1a and Vt2a of the test strips T1 and T2 are higher than the different-side terminal voltages Vt1b and Vt2b. The direction of a current flowing through the test strips T1 and T2 is thereby selected as direction A that allows the current to flow from the one-side terminals T1a and T2a to the different-side terminals T1b and T2b.

The controller 10 further controls the first D/A converter DAC1 and the second D/A converter DAC2 so that the one-side terminal voltages Vt1a and Vt2a of the test strips T1 and T2 are lower than the different-side terminal voltages Vt1b and Vt2b. The direction of a current flowing through the test strips T1 and T2 is thereby selected as direction B that allows the current to flow from the different-side terminals T1b and T2b to the one-side terminals T1a and T2a.

Configurations of the A/D converter ADC and the switches SW1 and SW2 are similar to those of the third embodiment.

The description below explains operation of the impedance measuring semiconductor circuit 4 according to the fourth embodiment. FIG. 11 is a diagram illustrating operation of the impedance measuring semiconductor circuit 4 according to the fourth embodiment. As illustrated in FIG. 11, the operation of the impedance measuring semiconductor circuit 4 will be described according to a first case, a second case, a third case, and a fourth case. The first case uses direction A as the current direction and adjusts the first D/A converter DAC1 to thereby provide control so that the terminal-to-terminal voltage Vt1 approximates to the target value Vtarget. The second case uses direction B as the current direction and adjusts the first D/A converter DAC1 to thereby provide control so that the terminal-to-terminal voltage Vt1 approximates to the target value Vtarget. The third case uses direction A as the current direction and adjusts the second D/A converter DAC2 to thereby provide control so that the terminal-to-terminal voltage Vt1 approximates to the target value Vtarget. The fourth case uses direction B as the current direction and adjusts the second D/A converter DAC2 to thereby provide control so that the terminal-to-terminal voltage Vt1 approximates to the target value Vtarget. The first case will be described first.

Figure 12:
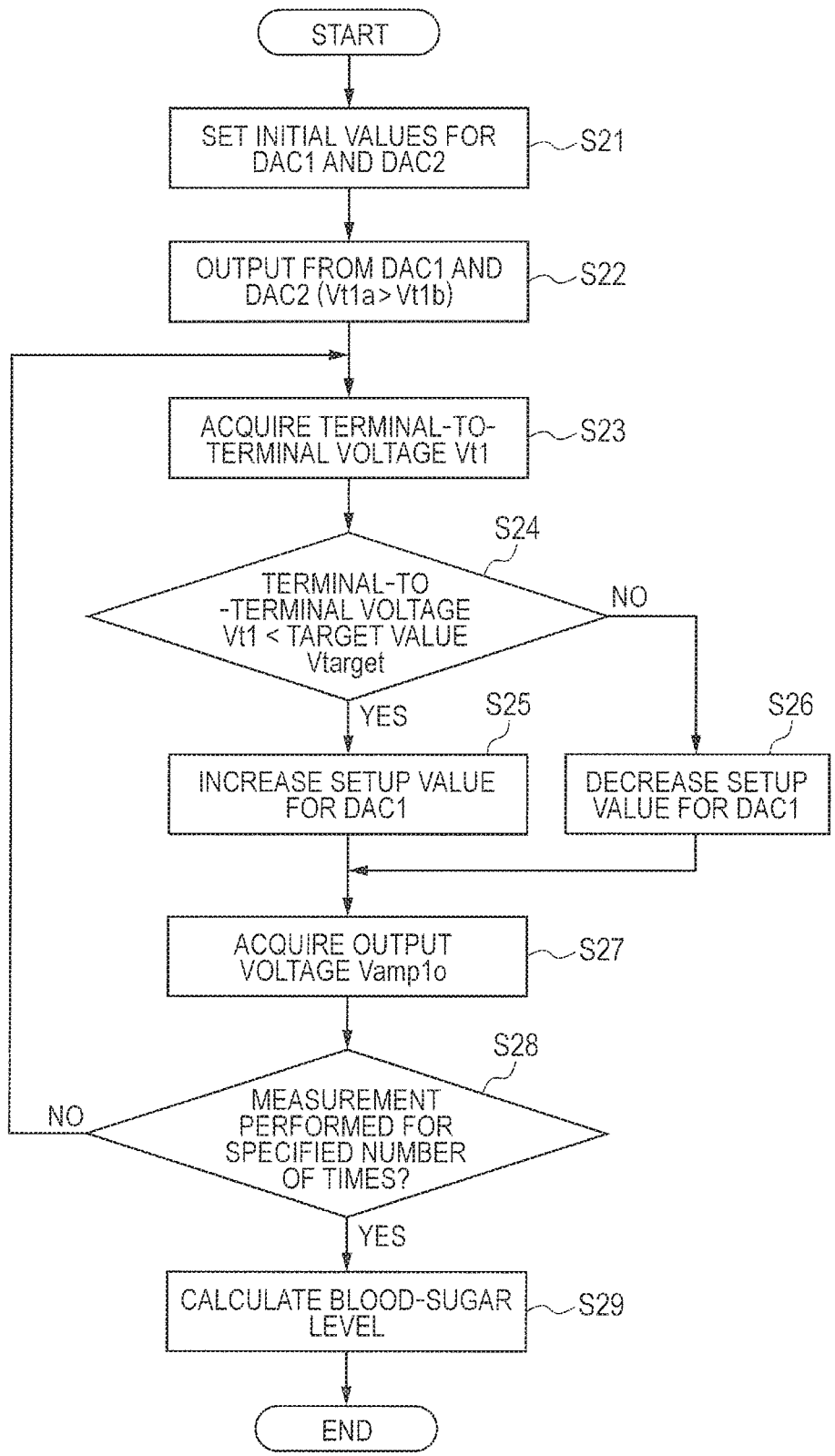
FIG. 12 is a flowchart illustrating operation of the impedance measuring semiconductor circuit according to the fourth embodiment in a first case.

FIG. 12 is a flowchart illustrating operation of the impedance measuring semiconductor circuit according to the fourth embodiment in the first case. The test strip T1 is used as a specimen. The same applies to the other specimens than the test strip T1.

At step S21 in FIG. 12, the controller 10 sets initial values for output voltages from the first D/A converter DAC1 and the second D/A converter DAC2. A potential difference between the initial value for the first D/A converter DAC1 and the initial value for the second D/A converter DAC2 corresponds to the target value Vtarget to be applied to the test strip T1.

At step S22, the controller 10 controls the first D/A converter DAC1 to output the initial value set for the first D/A converter DAC1. The controller 10 controls the second D/A converter DAC2 to output the initial value set for the second D/A converter DAC2.

The first D/A converter DAC1 thereby outputs the initial value to the positive output terminal of the operational amplifier AMP1. The second D/A converter DAC2 outputs the initial value to the positive output terminal of the buffer amplifier AMP2.

The virtual ground of the operational amplifier AMP1 supplies the test strip T1 with a differential voltage between the output voltage from the first D/A converter DAC1 and the output voltage from the second D/A converter DAC2.

In the first case, the controller 10 controls at least one of the first D/A converter DAC1 and the second D/A converter DAC2 so that the one-side terminal voltage Vt1a is higher than the different-side terminal voltage Vt1b. The current direction is then selected as direction A from the one-side terminal T1a to the different-side terminal T1b. In the first case, the controller 10 favorably controls the first D/A converter DAC1 so that the one-side terminal voltage Vt1a is higher than the different-side terminal voltage Vt1b. Only the first D/A converter DAC1 needs to be controlled and the control is facilitated.

Before a current flows through the test strip T1, a differential voltage between the initial value for the first D/A converter DAC1 and the initial value for the second D/A converter DAC2 is applied between the test strip T1 and the switch SW1.

Immediately after that, a current starts to flow between the test strip T1 and the switch SW1. This causes a voltage drop due to the on-resistance of the switch SW1. The test strip T1 is therefore applied with a voltage acquired by subtracting the voltage drop at the switch SW1 from the differential voltage between the first and second D/A converters DAC1 and DAC2. The A/D converter ADC measures the one-side terminal voltage Vt1a of the test strip T1.

At step S23, the controller 10 acquires the terminal-to-terminal voltage Vt1 of the test strip T1. For example, the controller 10 calculates the terminal-to-terminal voltage Vt1 by using the one-side terminal voltage Vt1a measured by the A/D converter ADC and the output voltage from the second D/A converter DAC2.

At step S24, the controller 10 determines whether the acquired terminal-to-terminal voltage Vt1 is lower than the target value Vtarget. The terminal-to-terminal voltage Vt1 may be lower than the target value Vtarget (Yes). In this case, at step S25 and as illustrated in FIG. 11, the controller 10 controls the first D/A converter DAC1 so as to increase the setup value for the first D/A converter DAC1. The output voltage from the first D/A converter DAC1 is thereby increased.

At step S24, the terminal-to-terminal voltage Vt1 may be higher than or equal to the target value Vtarget (No). In this case, at step S26 and as illustrated in FIG. 11, the controller 10 controls the first D/A converter DAC1 so as to decrease the setup value for the first D/A converter DAC1. The output voltage from the first D/A converter DAC1 is thereby decreased.

At step S27, the controller 10 uses the A/D converter ADC to acquire the output voltage Vamp1o from the operational amplifier AMP1. The impedance measuring semiconductor circuit 4 measures the impedance of the specimen by using the output voltage Vamp1o from the operational amplifier AMP1.

At step S28, the controller 10 determines whether the measurement is performed for a specified number of times. When the measurement is not performed for a specified number of times (No), the process returns to step S23 and uses the A/D converter ADC to acquire the terminal-to-terminal voltage Vt1 of the test strip T1. The process is repeated from step S23 to step S28. Repeating the process at a specified interval can approximate the terminal-to-terminal voltage Vt1 applied to both ends of the test strip T1 to the target value Vtarget.

At step S28, the measurement may be performed for a specified number of times (Yes). In this case, the process proceeds to step S29 and calculates a blood-sugar level. For example, the operation part calculates the blood-sugar level correlated to the charge amount based on the graph as illustrated in FIG. 2. The process then restarts from step S21 when there is a need to measure other quantities such as a hematocrit value at the test strip T1. When the measurement on the test strip T1 terminates, the switch SW1 is turned off and the switch SW for a test strip other than the test strip T1 is turned on to continue measuring the test strip. A sequence of measuring test strips is not limited. The test strip T1 may be measured after measurement of a test strip other than the test strip T1. The other sequences may also be available.

Figure 13:
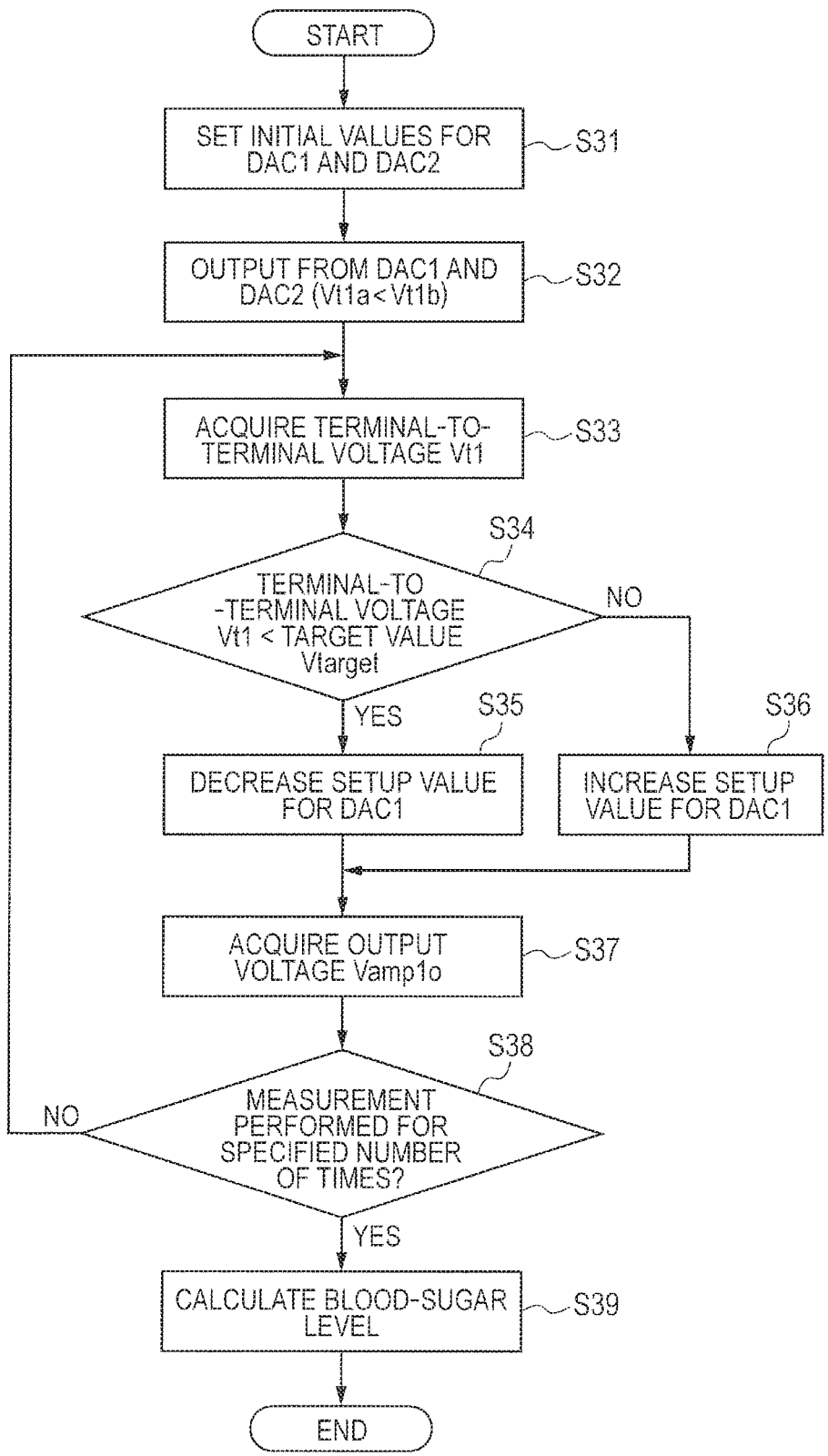
FIG. 13 is a flowchart illustrating operation of the impedance measuring semiconductor circuit according to the fourth embodiment in a second case.

The description below explains operation of the impedance measuring semiconductor circuit according to the fourth embodiment in the second case. FIG. 13 is a flowchart illustrating the operation of the impedance measuring semiconductor circuit according to the fourth embodiment in the second case. The test strip T1 is used as a specimen. The same applies to the other specimens than the test strip T1.

At step S31 in FIG. 13, the controller 10 sets initial values for output voltages from the first D/A converter DAC1 and the second D/A converter DAC2. A potential difference between the initial value for the first D/A converter DAC1 and the initial value for the second D/A converter DAC2 corresponds to the target value Vtarget to be applied to the test strip T1.

At step S32, the controller 10 controls the first D/A converter DAC1 to output the initial value set for the first D/A converter DAC1. The controller 10 controls the second D/A converter DAC2 to output the initial value set for the second D/A converter DAC2.

The first D/A converter DAC1 thereby outputs the initial value to the positive output terminal of the operational amplifier AMP1. The second D/A converter DAC2 outputs the initial value to the positive output terminal of the buffer amplifier AMP2.

The virtual ground of the operational amplifier AMP1 supplies the test strip T1 with a differential voltage between the output voltage from the first D/A converter DAC1 and the output voltage from the second D/A converter DAC2.

In the second case, the controller 10 controls at least one of the first D/A converter DAC1 and the second D/A converter DAC2 so that the one-side terminal voltage Vt1a is lower than the different-side terminal voltage Vt1b. The current direction is then selected as direction B from the different-side terminal T1b to the one-side terminal T1a. In the second case, the controller 10 favorably controls the first D/A converter DAC1 so that the one-side terminal voltage Vt1a is lower than the different-side terminal voltage Vt1b. Only the first D/A converter DAC1 needs to be controlled and the control is facilitated.

A current starts to flow between the test strip T1 and the switch SW1, and then a voltage drop occurs due to the on-resistance of the switch SW1. The test strip T1 is therefore applied with a voltage acquired by subtracting the voltage drop at the switch SW1 from the differential voltage between the first and second D/A converters DAC1 and DAC2. The A/D converter ADC measures the one-side terminal voltage Vt1a of the test strip T1.

At step S33, the controller 10 acquires the terminal-to-terminal voltage Vt1 of the test strip T1. For example, the controller 10 calculates the terminal-to-terminal voltage Vt1 by using the one-side terminal voltage Vt1a measured by the A/D converter ADC and the output voltage from the second D/A converter DAC2.

At step S34, the controller 10 determines whether the acquired terminal-to-terminal voltage Vt1 is lower than the target value Vtarget. The terminal-to-terminal voltage Vt1 may be lower than the target value Vtarget (Yes). In this case, at step S35 and as illustrated in FIG. 11, the controller 10 controls the first D/A converter DAC1 so as to decrease the setup value for the first D/A converter DAC1. The output voltage from the first D/A converter DAC1 is thereby decreased.

At step S34, the terminal-to-terminal voltage Vt1 may be higher than or equal to the target value Vtarget (No). In this case, at step S36 and as illustrated in FIG. 11, the controller 10 controls the first D/A converter DAC1 so as to increase the setup value for the first D/A converter DAC1. The output voltage from the first D/A converter DAC1 is thereby increased. Step S37 through step S39 are similar to step S27 through step S29 as above.

Figure 14:
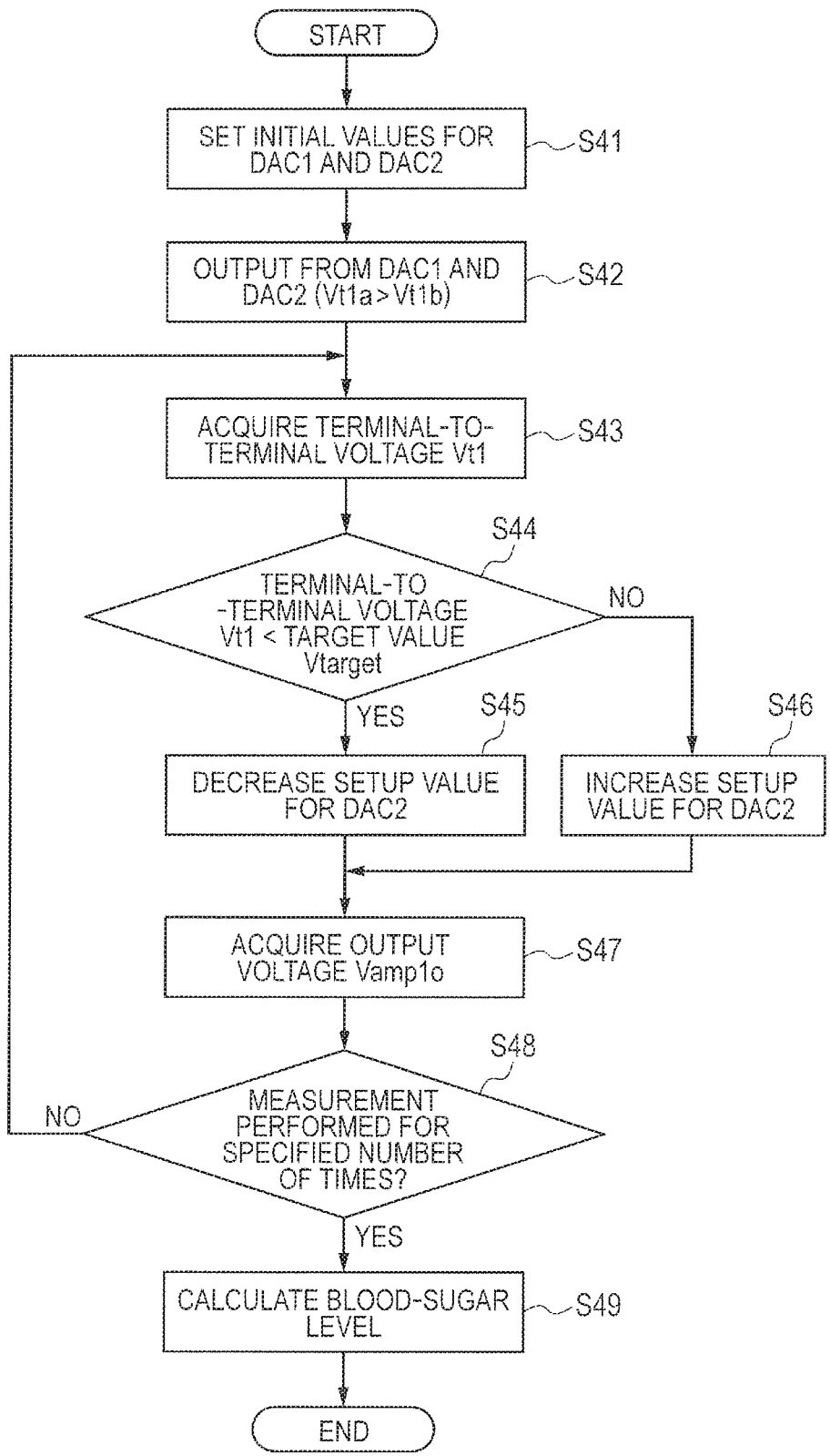
FIG. 14 is a flowchart illustrating operation of the impedance measuring semiconductor circuit according to the fourth embodiment in a third case.

The description below explains operation of the impedance measuring semiconductor circuit according to the fourth embodiment in the third case. FIG. 14 is a flowchart illustrating the operation of the impedance measuring semiconductor circuit according to the fourth embodiment in the third case. The test strip T1 is used as a specimen. The same applies to the other specimens than the test strip T1.

At step S41 in FIG. 14, the controller 10 sets initial values for output voltages from the first D/A converter DAC1 and the second D/A converter DAC2. A potential difference between the initial value for the first D/A converter DAC1 and the initial value for the second D/A converter DAC2 corresponds to the target value Vtarget to be applied to the test strip T1.

At step S42, the controller 10 controls the first D/A converter DAC1 to output the initial value set for the first D/A converter DAC1. The controller 10 controls the second D/A converter DAC2 to output the initial value set for the second D/A converter DAC2.

The first D/A converter DAC1 thereby outputs the initial value to the positive output terminal of the operational amplifier AMP1. The second D/A converter DAC2 outputs the initial value to the positive output terminal of the buffer amplifier AMP2.

The virtual ground of the operational amplifier AMP1 supplies the test strip T1 with a differential voltage between the output voltage from the first D/A converter DAC1 and the output voltage from the second D/A converter DAC2.

In the third case, the controller 10 controls at least one of the first D/A converter DAC1 and the second D/A converter DAC2 so that the one-side terminal voltage Vt1a is higher than the different-side terminal voltage Vt1b. The current direction is then selected as direction A from the one-side terminals T1a and T2a to the different-side terminals T1b and T2b. In the third case, the controller 10 favorably controls the second D/A converter DAC2 so that the one-side terminal voltage Vt1a is higher than the different-side terminal voltage Vt1b. Only the second D/A converter DAC2 needs to be controlled and the control is facilitated.

A current starts to flow between the test strip T1 and the switch SW1, and then a voltage drop occurs due to the on-resistance of the switch SW1. The test strip T1 is therefore applied with a voltage acquired by subtracting the voltage drop at the switch SW1 from the differential voltage between the first and second D/A converters DAC1 and DAC2. The A/D converter ADC measures the one-side terminal voltage Vt1a of the test strip T1.

At step S43, the controller 10 acquires the terminal-to-terminal voltage Vt1 of the test strip T1. For example, the controller 10 calculates the terminal-to-terminal voltage Vt1 by using the one-side terminal voltage Vt1a measured by the A/D converter ADC at the test strip T1 and the output voltage from the second D/A converter DAC2.

At step S44, the controller 10 determines whether the acquired terminal-to-terminal voltage Vt1 is lower than the target value Vtarget. The terminal-to-terminal voltage Vt1 may be lower than the target value Vtarget (Yes). In this case, at step S45 and as illustrated in FIG. 11, the controller 10 controls the second D/A converter DAC2 so as to decrease the setup value for the second D/A converter DAC2. The output voltage from the second D/A converter DAC2 is thereby decreased.

At step S44, the terminal-to-terminal voltage Vt1 may be higher than or equal to the target value Vtarget (No). In this case, at step S46 and as illustrated in FIG. 11, the controller 10 controls the second D/A converter DAC2 so as to increase the setup value for the second D/A converter DAC2. The output voltage from the second D/A converter DAC2 is thereby increased. Step S47 through step S49 are similar to step S27 through step S29 as above.

Figure 15:
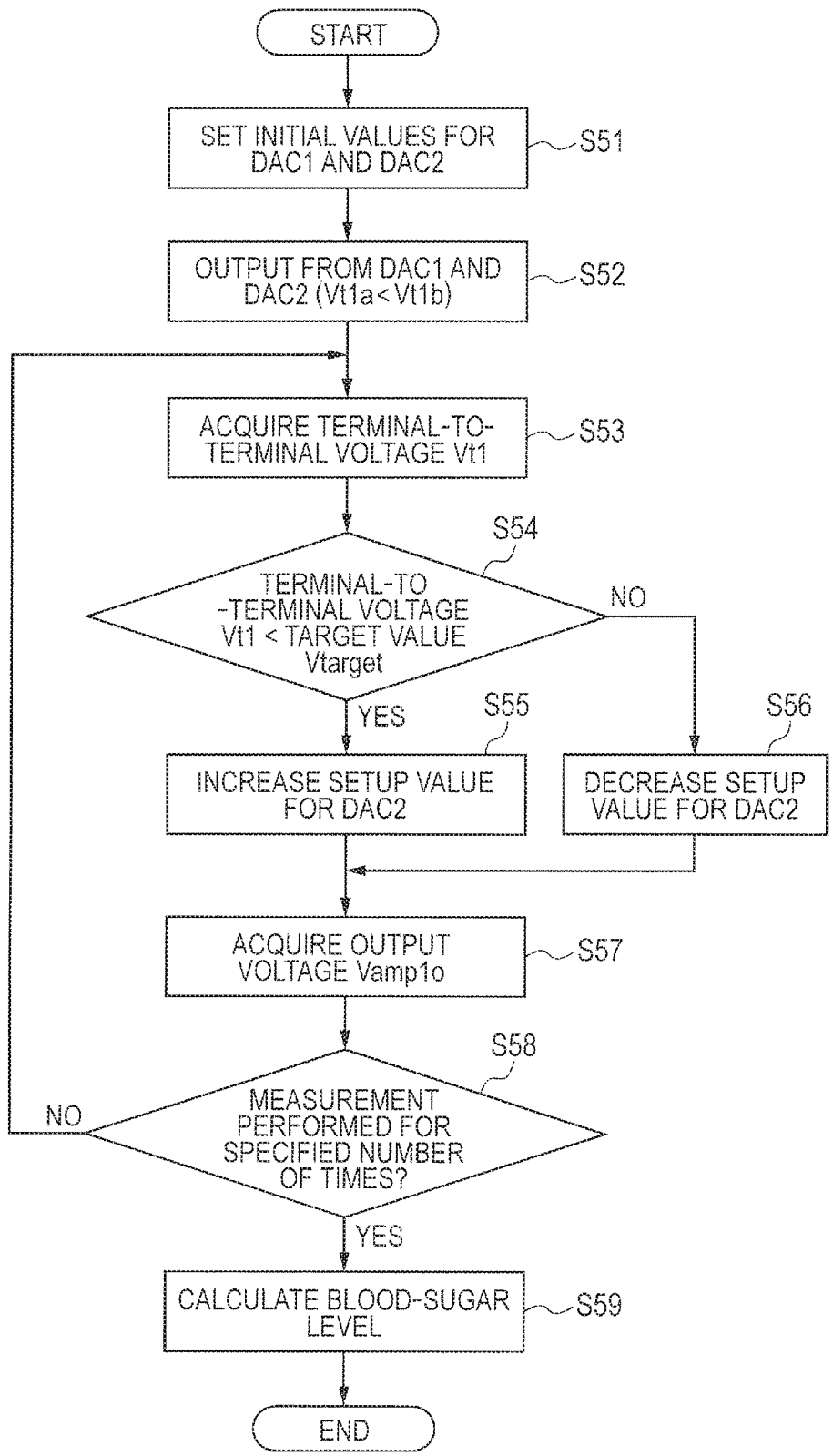
FIG. 15 is a flowchart illustrating operation of the impedance measuring semiconductor circuit according to the fourth embodiment in a fourth case.

The description below explains operation of the impedance measuring semiconductor circuit according to the fourth embodiment in the fourth case. FIG. 15 is a flowchart illustrating the operation of the impedance measuring semiconductor circuit according to the fourth embodiment in the fourth case. The test strip T1 is used as a specimen. The same applies to the other specimens than the test strip T1.

At step S51 in FIG. 15, the controller 10 sets initial values for output voltages from the first D/A converter DAC1 and the second D/A converter DAC2. A potential difference between the initial value for the first D/A converter DAC1 and the initial value for the second D/A converter DAC2 corresponds to the target value Vtarget to be applied to the test strip T1.

At step S52, the controller 10 controls the first D/A converter DAC1 to output the initial value set for the first D/A converter DAC1. The controller 10 controls the second D/A converter DAC2 to output the initial value set for the second D/A converter DAC2.

The first D/A converter DAC1 thereby outputs the initial value to the positive output terminal of the operational amplifier AMP1. The second D/A converter DAC2 outputs the initial value to the positive output terminal of the buffer amplifier AMP2.

The virtual ground of the operational amplifier AMP1 supplies the test strip T1 with a differential voltage between the output voltage from the first D/A converter DAC1 and the output voltage from the second D/A converter DAC2.

In the fourth case, the controller 10 controls at least one of the first D/A converter DAC1 and the second D/A converter DAC2 so that the one-side terminal voltage Vt1a is lower than the different-side terminal voltage Vt1b. The current direction is then selected as direction B from the different-side terminal T1b to the one-side terminal T1a. In the fourth case, the controller 10 favorably controls the second D/A converter DAC2 so that the one-side terminal voltage Vt1a is lower than the different-side terminal voltage Vt1b. Only the second D/A converter DAC2 needs to be controlled and the control is facilitated.

A current starts to flow between the test strip T1 and the switch SW1, and then a voltage drop occurs due to the on-resistance of the switch SW1. The test strip T1 is therefore applied with a voltage acquired by subtracting the voltage drop at the switch SW1 from the differential voltage between the first and second D/A converters DAC1 and DAC2. The A/D converter ADC measures the one-side terminal voltage Vt1a of the test strip T1.

At step S53, the controller 10 acquires the terminal-to-terminal voltage Vt1 of the test strip T1. For example, the controller 10 calculates the terminal-to-terminal voltage Vt1 by using the one-side terminal voltage Vt1a measured by the A/D converter ADC and the output voltage from the second D/A converter DAC2.

At step S54, the controller 10 determines whether the acquired terminal-to-terminal voltage Vt1 is lower than the target value Vtarget. The terminal-to-terminal voltage Vt1 may be lower than the target value Vtarget (Yes). In this case, at step S55 and as illustrated in FIG. 11, the controller 10 controls the second D/A converter DAC2 so as to increase the setup value for the second D/A converter DAC2. The output voltage from the second D/A converter DAC2 is thereby increased.

At step S54, the terminal-to-terminal voltage Vt1 may be higher than or equal to the target value Vtarget (No). In this case, at step S56 and as illustrated in FIG. 11, the controller 10 controls the second D/A converter DAC2 so as to decrease the setup value for the second D/A converter DAC2. The output voltage from the second D/A converter DAC2 is thereby decreased. Step S57 through step S59 are similar to step S27 through step S29 as above.

The process then terminates. As above, the impedance measuring semiconductor circuit 1 measures the impedance of the test strip T1 as a specimen.

Figure 16:
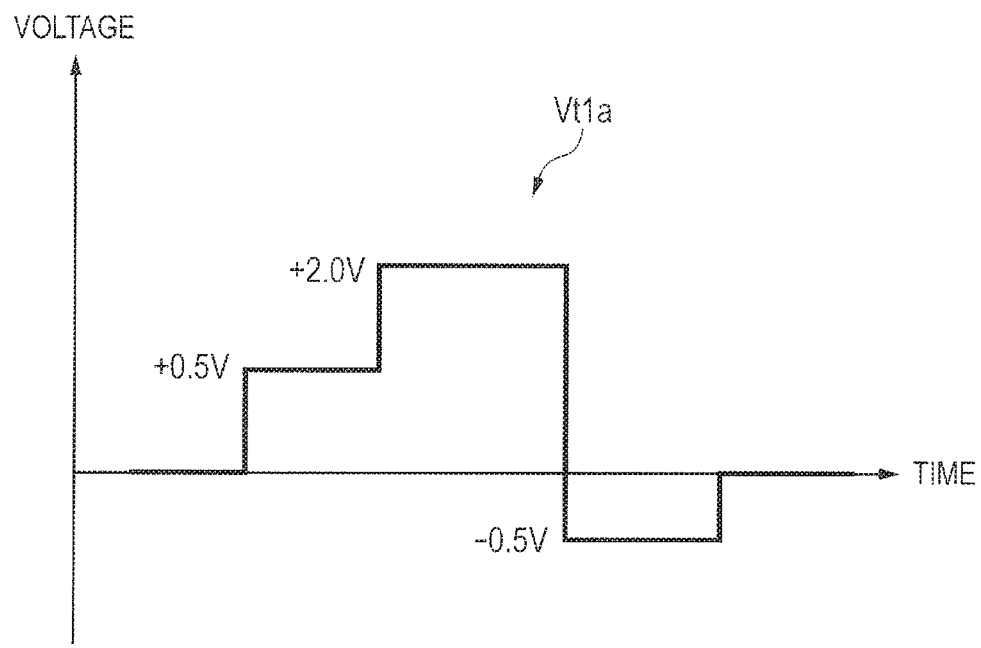
FIG. 16 is a graph illustrating operation of the impedance measuring semiconductor circuit according to the fourth embodiment, in which the horizontal axis represents the time and the vertical axis represents a voltage at one-side terminal of a test strip.
Figure 17:
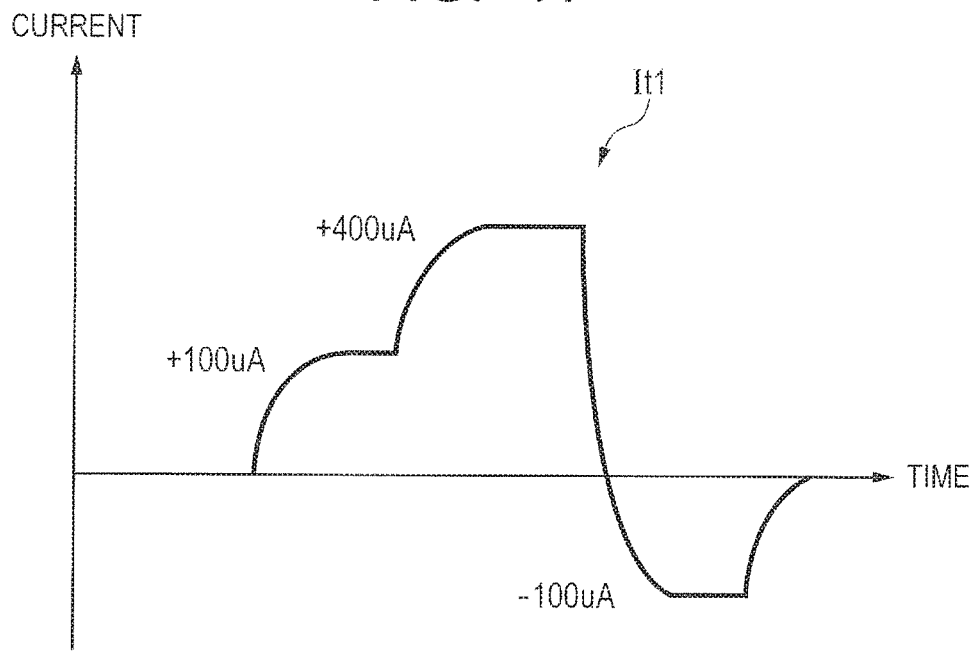
FIG. 17 is a graph illustrating operation of the impedance measuring semiconductor circuit according to the fourth embodiment, in which the horizontal axis represents the time and the vertical axis represents a current flowing through a test strip.

FIG. 16 is a graph illustrating operation of the impedance measuring semiconductor circuit according to the fourth embodiment, in which the horizontal axis represents the time and the vertical axis represents a voltage at the one-side terminal of the test strip T1. FIG. 17 is a graph illustrating operation of the impedance measuring semiconductor circuit according to the fourth embodiment, in which the horizontal axis represents the time and the vertical axis represents a current flowing through a test strip.

The present embodiment can also measure other substances such as a hematocrit value other than the blood-sugar level at the test strip T1. The present embodiment can stepwise vary a voltage applied to the test strip T1 and reverse a current.

As illustrated in FIGS. 16 and 17, for example, the blood-sugar level measurement uses the one-side terminal voltage Vt1a of +0.5[V] as a target value. In this case, a current of +100[μA] flows through the test strip T1. The hematocrit value measurement uses the one-side terminal voltage Vt1a of +2.0[V] as a target value. In this case, a current of +400[μA] flows through the test strip T1. Except blood-sugar levels and hematocrit values, the one-side terminal voltage Vt1a of −0.5 [V] is used as a target value. In this case, a current of −100 [μA] flows through the test strip T1.

Effects of the present embodiment will be described. The impedance measuring semiconductor circuit 4 according to the present embodiment can control each of the first D/A converter DAC1 and the second D/A converter DAC2. The terminal-to-terminal voltage Vt1 applied to both ends of the test strip T1 can be therefore set to discretionary values. It is possible to versatilely control the magnitude and the direction of the current It1 flowing through the test strip T1.

Voltages to be applied may vary with substances or enzyme to be measured. There may be a case where a negative voltage is applied. The present embodiment can versatily control the magnitude and the direction of the terminal-to-terminal voltage Vt1 at the test strip T1 and is therefore applicable to a case where a voltage to be applied varies with a substance or enzyme to be measured.

While there have been described the specific embodiments of the invention made by the inventors, it is to be distinctly understood that the present invention is not limited to the above-mentioned embodiments and may be embodied in various modifications without departing from the spirit and scope of the invention.

For example, a blood-sugar level meter including the impedance measuring semiconductor circuit according to the above-mentioned embodiments also falls within the scope of the technical idea of the embodiments. Effects of such a blood-sugar level meter are included in the description of the first through fourth embodiments. The above-mentioned embodiments measure the one-side terminal voltage Vt1a and the terminal-to-terminal voltage Vt1 of the test strip T1, for example, and control an output voltage from the D/A converter DAC1, for example, based on the values. Alternatively, it may be possible to detect an anomaly or diagnose degradation of a sensor included in the test strip T1 by measuring whether the one-side terminal voltage Vt1a and the terminal-to-terminal voltage Vt1 of the test strip T1 being measured, for example, exceed a predetermined threshold value.

What is claimed is:

1. An impedance measuring semiconductor circuit comprising:
    a first test strip including a first one-side terminal and a first different-side terminal, the first test strips including a first specimen;
    a second test strip including a second one-side terminal and a second different-side terminal, the second test strips including a second specimen;
    an operational amplifier;
    a resistance coupled between a negative input terminal of the operational amplifier and an output terminal of the operational amplifier;
    a D/A converter coupled to a positive input terminal of the operational amplifier;
    a first switch placed between the first one-side terminal of the first test strip and the negative input terminal of the operational amplifier;
    a second switch placed between the second one-side terminal of the second test strip and the negative input terminal of the operational amplifier;
    an A/D converter that is coupled with the output terminal of the operational amplifier, the first one-side terminal of the first test strip, and the second one-side terminal of the second test strip, and that measures an output voltage from the operational amplifier, a first one-side terminal voltage as a terminal voltage of the first one-side terminal, and a second one-side terminal voltage as a terminal voltage of the second one-side terminal; and
    a controller that 1) sets the first one-side terminal voltage and the second one-side terminal voltage to a target value to measure a first substance in the first specimen and the second specimen, 2) varies the target value in a stepwise manner to measure a second substance in the first specimen and the second specimen, and 3) controls an output voltage from the D/A converter based on the first one-side terminal voltage and the second one-side terminal voltage measured by the A/D converter,
    wherein a first different-side terminal voltage as a terminal voltage of the first different-side terminal and a second different-side terminal voltage as a terminal voltage of the second different-side terminal are set to a predetermined voltage, and
    wherein the output voltage from the operational amplifier is used to measure first impedance of the first specimen and second impedance of the second specimen.

2. The impedance measuring semiconductor circuit according to claim 1, wherein the first different-side terminal voltage and the second different-side terminal voltage are grounded to be set to a predetermined voltage.

3. The impedance measuring semiconductor circuit according to claim 1, wherein the controller 1) increases the output voltage from the D/A converter in case of the first one-side terminal voltage or the second one-side terminal voltage is lower than the target value and 2) decreases the output voltage from the D/A converter in case of the first one-side terminal voltage or the second one-side terminal voltage is higher than or equal to the target value.

4. The impedance measuring semiconductor circuit according to claim 1, further comprising:
    a buffer amplifier that includes an output terminal and a negative input terminal coupled to each other, and that is supplied with a reference voltage at a positive input terminal of the buffer amplifier,
    wherein the first different-side terminal voltage and the second different-side terminal voltage are set to a predetermined voltage by being coupled to the output terminal of the buffer amplifier.

5. The impedance measuring semiconductor circuit according to claim 4, wherein the controller controls the D/A converter to cause the first one-side terminal voltage to be lower than the first different-side terminal voltage and the second one-side terminal voltage to be lower than the second different-side terminal voltage.

6. The impedance measuring semiconductor circuit according to claim 1, wherein at least one of the operational amplifier, the A/D converter, the D/A converter, the first switch, and the second switch includes a CMOS structure formed over a semiconductor substrate.

7. The impedance measuring semiconductor circuit according to claim 1, wherein the first test strip and the second test strip each includes a sensor whose electrode is applied with enzyme.

8. The impedance measuring semiconductor circuit according to claim 1, further comprising:
    an operation part that calculates a blood-sugar level of the first specimen from the measured first impedance and a blood-sugar level of the second specimen from the measured second impedance.

9. A blood-sugar level meter comprising the impedance measuring semiconductor circuit according to claim 1.

10. An impedance measuring semiconductor circuit comprising:
    a first test strip including a first one-side terminal and a first different-side terminal, the first test strips including a first specimen;
    a second test strip including a second one-side terminal and a second different-side terminal, the second test strips including a second specimen;
    an operational amplifier;
    a resistance coupled between a negative input terminal of the operational amplifier and an output terminal of the operational amplifier;
    a first D/A converter coupled to a positive input terminal of the operational amplifier;

a first switch placed between the first one-side terminal of the first test strip and the negative input terminal of the operational amplifier;

a second switch placed between the second one-side terminal of the second test strip and the negative input terminal of the operational amplifier;

an A/D converter that is coupled with the output terminal of the operational amplifier, the first one-side terminal of the first test strip, and the second one-side terminal of the second test strip, and that measures an output voltage from the operational amplifier, a first one-side terminal voltage as a terminal voltage of the first one-side terminal, and a second one-side terminal voltage as a terminal voltage of the second one-side terminal; and a buffer amplifier that includes an output terminal and a negative input terminal coupled to each other;

a second D/A converter coupled to a positive input terminal of the buffer amplifier; and a controller that 1) sets i) the first terminal-to-terminal voltage between the first one-side terminal and the first different-side terminal and ii) the second terminal-to-terminal voltage between the second one-side terminal and the second different-side terminal to a target value to measure a first substance in the first specimen and the second specimen, 2) varies the target value in a stepwise manner to measure a second substance in the first specimen and the second specimen, and 3) controls at least one of an output voltage from the first D/A converter and an output voltage from the second D/A converter based on the first terminal-to-terminal voltage or the second terminal-to-terminal voltage, wherein the first terminal-to-terminal voltage and the second terminal-to-terminal voltage are calculated using the first one-side terminal voltage and the second one-side terminal voltage measured by the A/D converter, respectively, wherein the output voltage from the operational amplifier is used to measure first impedance of the first specimen and second impedance of the second specimen.

11. The impedance measuring semiconductor circuit according to claim 10, wherein the controller controls the first D/A converter to cause the first one-side terminal voltage to be higher than a first different-side terminal voltage as a terminal voltage of the first different-side terminal and cause the second one-side terminal voltage to be higher than a second different-side terminal voltage as a terminal voltage of the second different-side terminal.

12. The impedance measuring semiconductor circuit according to claim 11, wherein the controller 1) increases the output voltage from the first D/A converter in case of the first terminal-to-terminal voltage or the second terminal-to-terminal voltage being lower than the target value and 2) decreases an output voltage from the first D/A converter in case of the first terminal-to-terminal voltage or the second terminal-to-terminal voltage being higher than or equal to the target value.

13. The impedance measuring semiconductor circuit according to claim 10, wherein the controller controls the first D/A converter to cause the first one-side terminal voltage to be lower than a first different-side terminal voltage as a terminal voltage of the first different-side terminal and cause the second one-side terminal voltage to be lower than a second different-side terminal voltage as a terminal voltage of the second different-side terminal.

14. The impedance measuring semiconductor circuit according to claim 13, wherein the controller 1) decreases the output voltage from the first D/A converter in case of the first terminal-to-terminal voltage or the second terminal-to-terminal voltage being lower than the target value and 2) increases the output voltage from the first D/A converter in case of the first terminal-to-terminal voltage or the second terminal-to-terminal voltage being higher than or equal to the target value.

15. The impedance measuring semiconductor circuit according to claim 10, wherein the controller controls the second D/A converter to cause the first one-side terminal voltage to be higher than a first different-side terminal voltage as a terminal voltage of the first different-side terminal and the second one-side terminal voltage to be higher than a second different-side terminal voltage as a terminal voltage of the second different-side terminal.

16. The impedance measuring semiconductor circuit according to claim 15, wherein the controller 1) decreases an output voltage from the second D/A converter in case of the first terminal-to-terminal voltage or the second terminal-to-terminal voltage being lower than the target value and 2) increases an output voltage from the second D/A converter in case of the first terminal-to-terminal voltage or the second terminal-to-terminal voltage being higher than or equal to the target value.

17. The impedance measuring semiconductor circuit according to claim 10, wherein the controller controls the second D/A converter to cause the first one-side terminal voltage to be lower than a first different-side terminal voltage as a terminal voltage of the first different-side terminal and the second one-side terminal voltage to be lower than a second different-side terminal voltage as a terminal voltage of the second different-side terminal.

18. The impedance measuring semiconductor circuit according to claim 17, wherein the controller 1) increases the output voltage from the second D/A converter in case of the first terminal-to-terminal voltage or the second terminal-to-terminal voltage being lower than the target value and 2) decreases the output voltage from the second D/A converter in case of the first terminal-to-terminal voltage or the second terminal-to-terminal voltage being higher than or equal to the target value.

19. The impedance measuring semiconductor circuit according to claim 10, wherein at least one of the operational amplifier, the A/D converter, the first D/A converter, the second D/A converter, the first switch, and the second switch includes a CMOS structure formed over a semiconductor substrate.

* * * * *